United States Patent
Demirci et al.

(10) Patent No.: US 10,928,404 B2
(45) Date of Patent: Feb. 23, 2021

(54) SYSTEM AND METHOD FOR CELL LEVITATION AND MONITORING

(71) Applicants: THE BRIGHAM AND WOMEN'S HOSPITAL, Boston, MA (US); BOARD OF TRUSTEES OF THE LELAND STANFORD JUNIOR UNIVERSITY, Palo Alto, CA (US); BETH ISRAEL DEACONESS MEDICAL CENTER, Boston, MA (US)

(72) Inventors: Utkan Demirci, Stanford, CA (US); Ionita Ghiran, Boston, MA (US); Savas Tasoglu, Storrs, CT (US); Ronald W. Davis, Palo Alto, CA (US); Lars Steinmetz, Palo Alto, CA (US); Naside Gozde Durmus, Palo Alto, CA (US); Huseyin Cumhur Tekin, Palo Alto, CA (US)

(73) Assignees: The Brigham and Women's Hospital, Inc., Boston, MA (US); The Board of Trustees of the Leland Stanford Junior University, Stanford, CA (US); Beth Israel Deaconess Medical Center, Boston, MA (US)

(*) Notice: Subject to any disclaimer, the term of this patent is extended or adjusted under 35 U.S.C. 154(b) by 0 days.

(21) Appl. No.: 15/121,646

(22) PCT Filed: Feb. 26, 2015

(86) PCT No.: PCT/US2015/017705
§ 371 (c)(1),
(2) Date: Aug. 25, 2016

(87) PCT Pub. No.: WO2015/130913
PCT Pub. Date: Sep. 3, 2015

(65) Prior Publication Data
US 2016/0370386 A1 Dec. 22, 2016

Related U.S. Application Data

(60) Provisional application No. 61/944,707, filed on Feb. 26, 2014, provisional application No. 62/072,040, filed on Oct. 29, 2014.

(51) Int. Cl.
*B03C 1/32* (2006.01)
*G01N 33/80* (2006.01)
*G01N 15/06* (2006.01)
*G01N 15/10* (2006.01)
*B01L 3/00* (2006.01)
*G01N 27/76* (2006.01)
*G01N 33/487* (2006.01)
(Continued)

(52) U.S. Cl.
CPC ........ *G01N 33/80* (2013.01); *B01L 3/502715* (2013.01); *B01L 3/502761* (2013.01); *B03C 1/32* (2013.01); *C12N 13/00* (2013.01); *C12Q 1/18* (2013.01); *G01N 15/0656* (2013.01); *G01N 15/1031* (2013.01); *G01N 27/76* (2013.01); *G01N 33/487* (2013.01); *G01N 33/491* (2013.01); *G01N 33/574* (2013.01); *B01L 2200/0647* (2013.01); *B01L 2300/0654* (2013.01); *B01L 2300/0838* (2013.01); *B01L 2300/168* (2013.01); *B03C 2201/18* (2013.01); *B03C 2201/26* (2013.01); *G01N 2015/0053* (2013.01); *G01N 2015/1006* (2013.01); *G01N 2500/10* (2013.01); *G01N 2800/042* (2013.01); *G01N 2800/26* (2013.01); *G01N 2800/52* (2013.01); *G01N 2800/7042* (2013.01)

(58) Field of Classification Search
None
See application file for complete search history.

(56) References Cited

U.S. PATENT DOCUMENTS 4,226,534 A 10/1980 Kuck
4,508,625 A 4/1985 Graham
(Continued)

FOREIGN PATENT DOCUMENTS

EP 1694856 B1 10/2015
JP 2002086015 A 3/2002
(Continued)

OTHER PUBLICATIONS

Chang et al., The Analyst, 2008, vol. 133, pp. 233-240 (Year: 2008).*

(Continued)

*Primary Examiner* — Scott Long
*Assistant Examiner* — Evelyn Y Pyla
(74) *Attorney, Agent, or Firm* — Quarles & Brady LLP

(57) ABSTRACT

Magnetic cell levitation and cell monitoring systems and methods are disclosed. A method for separating a heterogeneous population of cells is performed by placing a microcapillary channel containing the heterogeneous population of cells in a magnetically-responsive medium in the disclosed levitation system and separating the cells by balancing magnetic and corrected gravitational forces on the individual cells. A levitation system is also disclosed, having a microscope on which the microcapillary channel is placed and a set of two magnets between which the microcapillary channel is placed. Additionally, a method for monitoring cellular processes in real-time using the levitation system is disclosed.

36 Claims, 18 Drawing Sheets

(51) Int. Cl.
*C12N 13/00* (2006.01)
*C12Q 1/18* (2006.01)
*G01N 33/49* (2006.01)
*G01N 33/574* (2006.01)
*G01N 15/00* (2006.01)

(56) References Cited

U.S. PATENT DOCUMENTS

| | | |
|---|---|---|
| 4,522,953 A | 6/1985 | Barby et al. |
| 5,852,298 A | 12/1998 | Hatakeyama et al. |
| 5,968,820 A | 10/1999 | Zborowski et al. |
| 6,120,735 A | 9/2000 | Zborowski et al. |
| 6,159,378 A | 12/2000 | Holman et al. |
| 6,190,870 B1 | 2/2001 | Schmitz et al. |
| 6,355,491 B1 | 3/2002 | Zhou et al. |
| 6,677,752 B1 | 1/2004 | Creighton, IV et al. |
| 6,716,642 B1 | 4/2004 | Wu et al. |
| 6,806,050 B2 | 10/2004 | Zhou et al. |
| 6,858,439 B1 | 2/2005 | Xu et al. |
| 6,878,542 B1 | 4/2005 | Smith et al. |
| 6,902,065 B2 | 6/2005 | Kimura et al. |
| 6,949,355 B2 | 9/2005 | Yamanishi et al. |
| 7,081,192 B1 | 7/2006 | Wang et al. |
| 7,166,443 B2 | 1/2007 | Walker et al. |
| 7,312,085 B2 | 12/2007 | Chou et al. |
| 7,437,913 B2 | 10/2008 | Djennati et al. |
| 7,713,923 B2 | 5/2010 | Genove et al. |
| 7,740,424 B2 | 6/2010 | Pardini et al. |
| 8,034,245 B1 | 10/2011 | Snezhko et al. |
| 8,465,987 B2 | 6/2013 | Park et al. |
| 8,721,936 B2 | 5/2014 | Mao et al. |
| 8,961,878 B2 | 2/2015 | Koser |
| 8,969,021 B2 | 3/2015 | Lin et al. |
| 8,980,568 B2 | 3/2015 | Lin et al. |
| 9,174,221 B2 | 11/2015 | Nishijima et al. |
| 9,217,131 B2 | 12/2015 | Lamish et al. |
| 9,278,353 B2 | 3/2016 | Smith et al. |
| 9,290,812 B2 | 3/2016 | Yamanishi et al. |
| 9,308,536 B2 | 4/2016 | Nishijima et al. |
| 9,322,804 B2 | 4/2016 | Whitesides et al. |
| 9,352,317 B2 | 5/2016 | Koser |
| 9,370,782 B2 | 6/2016 | Nishijima et al. |
| 9,389,211 B2 | 7/2016 | Duhr et al. |
| 9,409,265 B2 | 8/2016 | Whitesides et al. |
| 9,500,644 B2 | 11/2016 | Schilffarth et al. |
| 9,517,474 B2 | 12/2016 | Mao et al. |
| 9,546,392 B2 | 1/2017 | Lamish et al. |
| 9,551,706 B2 | 1/2017 | Phillips et al. |
| 9,556,485 B2 | 1/2017 | Lin et al. |
| 9,561,511 B2 | 2/2017 | Nishijima et al. |
| 2002/0187072 A1 | 12/2002 | Karp |
| 2004/0072278 A1 | 4/2004 | Chou et al. |
| 2006/0247862 A1 | 11/2006 | Arini et al. |
| 2007/0020612 A1 | 1/2007 | Van Agthoven et al. |
| 2007/0049696 A1 | 3/2007 | Gonzalez et al. |
| 2008/0074449 A1 | 3/2008 | Lee et al. |
| 2010/0285606 A1 | 11/2010 | Phillips et al. |
| 2011/0261446 A1 | 10/2011 | Dunsby |
| 2011/0286975 A1 | 11/2011 | Souza et al. |
| 2012/0040846 A1 | 2/2012 | Kassis |
| 2012/0214217 A1 | 8/2012 | Grogan et al. |
| 2012/0301883 A1 | 11/2012 | Pagano et al. |
| 2012/0305398 A1 | 12/2012 | Muller et al. |
| 2013/0133419 A1 | 5/2013 | Whitesides et al. |
| 2013/0314080 A1 | 11/2013 | Whitesides et al. |
| 2014/0120570 A1 | 5/2014 | Yu et al. |
| 2014/0248618 A1 | 9/2014 | Shaikh et al. |
| 2014/0342470 A1 | 11/2014 | Su et al. |
| 2014/0349329 A1 | 11/2014 | Whitesides et al. |
| 2016/0244714 A1 | 8/2016 | Spuhler et al. |
| 2016/0263574 A1 | 9/2016 | Smith et al. |
| 2016/0266026 A1 | 9/2016 | Koser |
| 2016/0296944 A1 | 10/2016 | Koser |
| 2017/0029782 A1 | 2/2017 | Mao et al. |
| 2017/0072405 A1 | 3/2017 | Mao et al. |
| 2017/0074871 A1 | 3/2017 | Campbell et al. |
| 2017/0089814 A1 | 3/2017 | Lin et al. |
| 2017/0121669 A1 | 5/2017 | Lamish et al. |

FOREIGN PATENT DOCUMENTS

| | | |
|---|---|---|
| JP | 2009097864 A | 5/2009 |
| WO | WO-9708557 A1 | 3/1997 |
| WO | 9727933 A1 | 8/1997 |
| WO | WO-9838293 A1 | 9/1998 |
| WO | WO-0050175 A1 | 8/2000 |
| WO | WO-0054882 A1 | 9/2000 |
| WO | WO-0212896 A1 | 2/2002 |
| WO | WO-0231505 A1 | 4/2002 |
| WO | WO-0231506 A1 | 4/2002 |
| WO | WO-2004109277 A1 | 12/2004 |
| WO | WO-2005105314 A1 | 11/2005 |
| WO | WO-2008008515 A2 | 1/2008 |
| WO | WO-2008127295 A2 | 10/2008 |
| WO | WO-2009006409 A2 | 1/2009 |
| WO | WO-2011038370 A1 | 3/2011 |
| WO | WO-2011071912 A1 | 6/2011 |
| WO | WO-2011089603 A1 | 7/2011 |
| WO | WO-2012057878 A1 | 5/2012 |
| WO | WO-2012075009 A1 | 6/2012 |
| WO | 2012142179 A2 | 10/2012 |
| WO | 2013037732 A1 | 3/2013 |
| WO | 2013044089 A1 | 3/2013 |
| WO | WO-2013037732 A1 | 3/2013 |
| WO | WO-2013188725 A1 | 12/2013 |
| WO | WO-2014004577 A1 | 1/2014 |
| WO | WO-2014008487 A2 | 1/2014 |
| WO | WO-2015058206 A1 | 4/2015 |
| WO | WO-2015128725 A1 | 9/2015 |
| WO | WO-2015130745 A1 | 9/2015 |
| WO | WO-2015130913 A1 | 9/2015 |
| WO | WO-2016077067 A2 | 5/2016 |
| WO | WO-2016183032 A1 | 11/2016 |
| WO | WO-2017027519 A1 | 2/2017 |
| WO | WO-2017059353 A1 | 4/2017 |

OTHER PUBLICATIONS

Nam et al., Analytical Chemistry, 2013, vol. 85, pp. 7316-7323 (Year: 2013).*

Plouffe et al, Biomicrofluidics, vol. 5, 013413 (2011) (Year: 2011).*

Watarai et al., Journal of Chromatography A, vol. 961 (2002), pp. 3-8 (Year: 2001).*

Alderman, et al., Binding of immunoglobulin classes to subpopulations of human red blood cells separated by density-gradient centrifugation. Blood. May 1980; 55(5); 817-822.

Baday, et al., Integrating cell phone imaging with magnetic levitation (i-LEV) for label-free blood analysis at the point-of-living. Small 2016, 12, No. 9, 1222-1229.

Beaugnon, et al., Levitation of water and organic substances in high static magnetic fields. J. Phys. III, EDP Sciences, 1991; 1(8): 1423-1428.

Berry, et al., Of flying frogs and levitrons. Eur. J. Phys. Jun. 4, 1997; 18: 307-313. Printed in the UK.

Bieche, et al., Quantitation of MYC Gene Expression in Sporadic Breast Tumors with a Real-Time Reverse Transcription-PCR Assay. Cancer Res Jun. 15, 1999, 59(12):2759-2765.

Brooks, et al., New opportunities in science, materials, and biological systems in the low-gravity (magnetic levitation) environment (invited). Journal of Applied Physics. May 1, 2000; 87(9): 6194-6199.

Catherall, et al., Cryogenically enhanced magneto-Archimedes levitation. New Journal of Physics, 2005; 7(118): 1-10.

Catherall, et al., Floating gold in cryogenic oxygen. Nature. Apr. 10, 2003. vol. 422, p. 579, doi:10.1038/422579a.

Chetouani, et al., Diamagnetic levitation with permanent magnet microarrays for precise contactless guiding and trapping of microdroplets and bioparticles in fluids. Conference paper, INTERMAG 2006, p. 106.

(56) References Cited

OTHER PUBLICATIONS

Chetouani, et al., Diamagnetic levitation with permanent magnets for contactless guiding and trapping of microdroplets and particles in Air and liquids. IEEE Transactions on Magnetics, vol. 42, No. 10, Oct. 2006.

Durmus, et al., Magnetic levitation of single cells. PNAS. Published online Jun. 29, 2015. E3661-E3668. Supplementary Information, pp. 1-12.

European Search Report dated Sep. 21, 2017 for EP Application No. 15755490.8.

Geim, A.,Everyone's Magnetism. Physics Today, Sep. 1998; 36-39.

Hirota, et al., Magneto-Archimedes separation and its application to the separation of biological materials. Physica B 346-347 (2004) 267-271.

Hirota, et al., Magneto-archimedes levitation and its application, Riken Review, 2002, pp. 159-161.

Hirschbein et al., Magnetic separations in chemistry and biochemistry. CHEMTECH. 1982; 12: 172-179.

Inci, et al., Multitarget, quantitative nanoplasmonic electrical field-enhanced resonating device (NE2RD) for diagnostics. PNAS, Jul. 20, 2015, E4354-E4363.

Inglis, et al., Microfluidic high gradient magnetic cell separation, Journal of Applied Physics 99, 08K101 (2006); doi: 10.1063/1.2165782.

Institute of Physics, Scientists Levitate Heaviest Elements With Help From Cold Oxygen, Science Daily, May 11, 2005, www.sciencedaily.com/releases/2005/05/050511084556.htm.

International Search Report dated May 27, 2015 for International Application No. PCT/US2015/017451.

Kimura, et al., Separation of Solid Polymers by Magneto-Archimedes Levitation. Chemistry Letters 2000, 29(11):1294-1295.

Lyuksyutov, et al., Trapping Microparticles With Strongly Inhomogeneous Magnetic Fields. Modern Physics Letters B. 2003; 17(17): 935-940.

Maki, et al., High-quality crystallization of lysozyme by magneto-Archimedes levitation in a superconducing magnet. Journal of Crystal growth, 2004; 261(4):p. 557-565.

Molday, et al., Immunospecific ferromagnetic iron-dextran reagents for the labeling and magnetic separation of cells. Journal of Immunological Methods, 52 (1982) 353-367.

Nandi, et al., Separation of Deoxyribonucleic acids by Hg(II) binding and Cs2SO4 density-gradient centrifugation. Biochemistry, Sep. 11, 1965; 4(9): 1687-1696.

Rinehart, et al., The effect of silver ion binding and pH on the buoyant density of DNA and its use in fractionating heterogeneous DNA. Biochimica et Biophysica Acta, 425(1976) 451-462.

Rowley, et al., Isolation of CD34+ cells from blood stem cell components using the Baxter Isolex system. Bone Marrow Transplantation, (1998) 21, 1253-1262.

Science News Staff., Floating Frogs. Science, Apr. 14, 1997. Retrieved from: http://www.sciencemag.org/news/1997/04/floating-frogs.

Shapiro, et al., Magnetic levitation as a platform for competitive protein-ligand binding assays. Analytical Chemistry, 84(14); Jul. 17, 2012, 6166-6172.

Simon, et al., Diamagnetic levitation: Flying frogs and floating magnets (invited). Journal of Applied Physics. 2000; 87(9): 6200-6204.

Simon, et al., Diamagnetically stabilized magnet levitation. Manuscript No. 12096, Mar. 29, 2001; pp. 1-37.

Tasoglu, et al., Guided and magnetic self-assembly of tunable magnetoceptive gels. Nature Communications, 5; Sep. 1, 2014, Article No. 4702.

Tasoglu, et al., Levitational image cytometry with temporal resolution. Advanced Materials. 2015, 27, 3901-3908.

Tasoglu, et al., Magnetic Levitational Assembly for Living Material Fabrication. Adv. Healthcare Mater. 2015, 4, 1469-1476.

Tasoglu, et al., Manipulating biological agents and cells in microscale volumes for applications in medicine. Chemical Society Reviews, 42(13); Jan. 1, 2013, pp. 5788-5808.

Tseng, et al., Assembly of a three-dimensional multitype bronchiole coculture model using magnetic levitation. Tissue Engineering Part C: Methods, 19(9); Sep. 1, 2013, 665-675.

Valles, Jr., et al.,Stable Magnetic Field Gradient Levitation of Xenopus laevis: Toward Low-Gravity Simulation.Biophysical Journal. Aug. 1997; 73: 1130-1133.

Wang, et al., Label-free detection of small-molecule-protein interactions by using nanowire nanosensors. PNAS, Mar. 1, 2005. 102(9), 3208-3212.

Watarai, et al., Magnetophoretic behavior of single polystyrene particles in aqueous manganese(II) chloride. Analytical sciences, Oct. 2001, vol. 17, 1233-1236.

Asakura, et al., Relationship Between Morphologic Characteristics of Sickle Cells and Method of Deoxygenation, Journal of Laboratory and Clinical Medicine, 1984, 104(6):987-994.

Bryan, et al., Measurement of Mass, Density, and Volume During the Cell Cycle of Yeast, PNAS, 2010, 107 (3):999-1004.

Bryan, et al., Measuring Single Cell Mass, Volume, and Density with Dual Suspended Microchannel Resonators, Lab on a Chip, 2014, 14:569-576.

Costa, et al., Complex Dynamics of Human Red Blood Cell Flickering: Alterations with In Vivo Aging, Phys. Rev. E Stat Nonlin Soft Matter Phys., 2008, 78(2 Pt 1):020901.

Dustin, A Dynamic View of the Immunological Synapse, Seminars in Immunology, 2005, 17:400-410.

Fearon, et al., Increased Expression of C3b Receptors on Polymorphonuclear Leukocytes Induced by Chemotactic Factors and by Purification Procedures, Journal of Immunology, 1983, 130(1):370-375.

Freedman, et al., Platelet-Monocyte Aggregates—Bridging Thrombosis and Inflammation, Circulation, 2002, 105:2130-2132.

Glodek, et al., Ligation of Complement Receptor 1 Increases Erythrocyte Membrane Deformability, Blood, 2010, 116 (26):6063-6071.

Grover, et al., Measuring Single-Cell Density, PNAS, 2011, 108(27):10992-10996.

Klinger, et al., Interaction of Hemoglobin with Ions, Binding of ATP to Human Hemoglobin Under Simulated In Vivo Conditions, Eur. J. Biochem., 1971, 18:171-177.

Kobayashi, et al., Optical Motion Control of Maglev Graphite, J. Am. Chem. Soc., 2012, 134:20593-20596.

Linderkamp, et al., Age Dependency of Red Blood Cell Deformability and Density: Studies in Transient Erythroblastopenia of Childhood, British Journal of Haematology, 1993, 83(1):125-129.

Lockett, et al., Analyzing Forensic Evidence Based on Density with Magnetic Levitation, Journal of Forensic Sciences, 2013, 58(1):40-45.

Maric, et al., Buoyant Density Gradient Fractionation and Flow Cytometric Analysis of Embryonic Rat Cortical Neurons and Progenitor Cells, Methods, 1998, 16(3):247-259.

Martin, et al., HL-60 Cells Induced to Differentiate Towards Neutrophils Subsequently Die Via Apoptosis, Clin. Exp. Immunol., 1990, 79:448-453.

Mirica, et al., Measuring Densities of Solids and Liquids Using Magnetic Levitation: Fundamentals, J. Am. Chem. Soc., 2009, 131:10049-10058.

Mirica, et al., Magnetic Levitation in the Analysis of Foods and Water, Journal of Agricultural and Food Chemistry, 2010, 58:6565-6569.

Mirica, et al., Using Magnetic Levitation for Three Dimensional Self-Assembly, Advanced Materials, 2011, 23:4134-4140.

Mrema, et al., Concentration and Separation of Erythrocytes Infected with Plasmodium Falciparum by Gradient Centrifugation, Bulletin of the World Health Organization, 1979, 57(1):133-138.

Pember, et al., Density Heterogeneity of Neutrophilic Polymorphonuclear Leukocytes: Gradient Fractionation and Relationship to Chemotactic Stimulation, Blood, 1983, 61(6):1105-1115.

Radisic, et al., Micro- and Nanotechnology in Cell Separation, International Journal of Nanomedicine, 2006, 1(1):3-14.

Rikken, et al., Manipulation of Micro- and Nanostructure Motion with Magnetic Fields, Soft Matter, 2014, 10:1295-1308.

(56) References Cited

OTHER PUBLICATIONS

Rodgers, et al., Cell Heterogeneity in Sickle Cell Disease: Quantitation of the Erythrocyte Density Profile, Journal of Laboratory and Clinical Medicine, 1985, 106(1):30-37.
Shen, et al., Label-Free Cell Separation Using a Tunable Magnetophoretic Repulsion Force, Analytical Chemistry, 2012, 84:3075-3081.
Winkleman, et al., A Magnetic Trap for Living Cells Suspended in a Paramagnetic Buffer, Applied Physics Letters, 2004, 85(12):2411-2413.
Winkleman, et al., Density-Based Diamagnetic Separation: Devices for Detecting Binding Events and for Collecting Unlabeled Diamagnetic Particles in Paramagnetic Solutions, Analytical Chemistry, 2007, 79(17):6542-6550.
Wolff, et al., Separation of HeLa Cells by Colloidal Silica Density Gradient Centrifugation, Journal of Cell Biology, 1972, 55:579-585.
Wyllie, et al., Hormone-Induced Cell Death—Purification and Properties of Thymocytes Undergoing Apoptosis After Glucocorticoid Treatment, Am J. Pathol., 1982, 109:78-87.
PCT International Search Report and Written Opinion, PCT/US2015/017705, dated Jun. 3, 2015.
European Patent Office, Extended European Search Report, Application No. 15756020.2, dated Oct. 4, 2017, 11 pages.
Intellectual Property Office of Singapore, Written Opinion, Application No. 11201607118P, dated Nov. 8, 2017, 6 pages.
State Intellectual Property Office of the People's Republic of China, First Office Action and Search Report, Application No. 201580022049.X, dated Dec. 12, 2017, 12 pages.
Eurasian Patent Office, Office Action, Application No. 201691698, dated Sep. 14, 2018, 3 pages.
Intellectual Property Office of Singapore, Written Opinion, Application No. 11201607118P, dated Oct. 12, 2018, 6 pages [English Language Translation Only].
China National Intellectual Property Administration, Second Office Action, Application No. 201580022049.X, dated Dec. 5, 2018, 22 pages.
Japan Patent Office, Notification of Reasons for Rejection, Application No. 2016-554626, dated Dec. 18, 2018, 7 pages [English Language Translation Only].
Japan Patent Office, Decision to Grant a Patent, Application No. 2016-554626, dated Nov. 11, 2019, 5 pages.
Israeli Patent Office, Office Action, Application No. 247445, dated Jun. 10, 2019, 6 pages.

\* cited by examiner

SYSTEM AND METHOD FOR CELL LEVITATION AND MONITORING

CROSS-REFERENCE TO RELATED APPLICATIONS

This application represents the U.S. national stage of PCT International Application No. PCT/US2015/017705 filed Feb. 26, 2015, which claims priority to U.S. Provisional Patent Application No. 61/944,707 filed Feb. 26, 2014 and further claims the benefit of U.S. Provisional Patent Application No. 62/072,040 filed on Oct. 29, 2014. The contents of these applications are incorporated by reference herein in their entirety for all purposes.

STATEMENT OF FEDERALLY SPONSORED RESEARCH OR DEVELOPMENT

The invention was made with Government support under contracts CBET 1150733 awarded by the National Science Foundation and R01 A1093282, R15 HL115556, R01EB015776-01A1, R21HL112114, R01 HL096795, and P01 HG000205 awarded by the National Institutes of Health. The Government has certain rights in the invention.

BACKGROUND

This disclosure relates to the levitation of a heterogeneous population of cells and, more specifically, to the separation of cells based on differences in magnetic susceptibilities between the cells and a suspending medium, and a balance between magnetic and corrected gravitational forces.

Magnetic levitation has been traditionally used for analyses of densities and magnetic susceptibilities of individual, macroscopic objects and as a means effective in separating foods, determining the fat content in milk, cheese, and peanut butter, comparing a variety of grains on the basis of their intrinsic densities, guiding self-assembly of objects, and characterizing forensic-related evidence. These earlier magnetic levitation-based experiments were performed using large setups that were not compatible with or geared towards microscopy.

A wide variety of cellular processes, both physiological and pathological, are accompanied by transient or permanent changes in a cell's volumetric mass density or magnetic signature due to formation or quenching of intracellular paramagnetic reactive species, for example reactive oxygen species (ROS) or reactive nitrogen species (RNS). These events include cell-cycle stage, differentiation, cell-death (apoptosis/necrosis), malignancy, disease state, activation, phagocytosis, in vivo and ex vivo cell aging, viral infection, and specific as well as non-specific responses to drugs.

SUMMARY OF THE INVENTION

There have been few attempts to measure with high precision the density of single living cells. One such technology involves nanofabricated, suspended microchannel resonators that offers low throughput, and the necessity to use a sophisticated pump mechanism to transfer cells between fluids with different densities. Therefore, reliable tools designed for high resolution, real-time monitoring and quantification of magnetic signatures and volumetric mass densities of cells will help elucidate the intricate cellular mechanisms.

The present invention overcomes the aforementioned drawbacks by providing a levitation system for cells that is compatible with microscopy devices and that separates cells based on a balance between corrected gravitational forces on the cell and magnetic forces induced by magnets. The corrected gravitational force is the gravitational force exerted on the cell, accounting for the comparative densities of the specific cell in the specific medium (that is, the buoyancy of the cell) as is outlined in greater detail in the detailed description section, below.

In accordance with one aspect of the present invention, a method for separating a heterogeneous population of cells is provided. The method includes the steps of loading a sample of the heterogeneous population of cells into a microcapillary channel containing a magnetically-responsive medium (for example, a paramagnetic medium, a diamagnetic medium, or a solution containing radicals capable of producing a sufficient environmental difference for separation), placing the microcapillary channel containing the sample of cells and the magnetically-responsive medium into a levitation system, and levitating the heterogeneous population of cells in the magnetically-responsive medium. The levitation system used is made up of a set of two magnets producing a magnetic field, with a space between the two magnets that is sized to receive the microcapillary channel. Additionally, the levitation system includes a microscopy device that has a stage between the set of two magnets on which the microcapillary channel is placed. The step of levitation of the cells occurs by balancing a magnetic force applied to each of the cells by the magnetic field of the magnets with a corrected gravitational force of the cells in the magnetically-responsive medium, which consequently separates the heterogeneous population of cells. The mechanism is contrary to those previously practiced, which have been known to balance magnetic force with inertial and drag forces rather than balancing magnetic forces with corrected gravitational forces.

In some specific forms, the heterogeneous population of cells may be selected from that of red blood cells, leukocytes, lymphocytes, phagocytes, platelets, cancer cells, and the like. It is also possible for the magnetically-responsive medium to be a paramagnetic medium and to comprise gadolinium or to be gadolinium based, where the medium can be pure gadolinium, or allow for additional constituents.

In a further possibility, the individual cells within the heterogeneous population of cells may be differentiated from others based on at least one of their magnetic susceptibility and cell density created by a cell variant. The cell variant may be caused by multiple differences between the cells such as cell type, cell-cycle stage, malignancy, disease state, activation state, cellular age, infection state, cellular differentiation, apoptosis of the cell, and phagocytosis of the cell.

In some forms, the magnetic field gradient may be created using electrical magnets. These electrical magnets may create the gradient using alternating currents. In some forms, the set of two magnets may be two permanent magnets in an anti-Helmholtz configuration.

In some forms, the separation of the individual cells may occur to an equilibrium exhibiting a balance between gravitational forces and magnetic forces on the individual cells.

Furthermore, it is possible for the separation of the population of cells to be performed at the point of care, as the levitation system being used does not interfere with mobile devices that can be used for remote diagnostics.

In some forms of the method, the method may further include the step of observing the heterogeneous population of cells in real time using the microscopy device and the microscopy device may provide various images of the heterogeneous population of cells over a duration of time.

Over this duration of time, further steps may be performed. For example, a physical environment of the heterogeneous population of cells may be altered and a response of the heterogeneous population of cells as a result of the physical environment may be observed. As another example, a treatment agent (such as for example, a drug or an antibiotic) may be introduced into the heterogeneous population of cells and a response of the heterogeneous population of cells as a result of the introduction of treatment agent may be observed. If a treatment agent is introduced, then the method can further include monitoring a continued response of the heterogeneous population of cells to establish the emergence of resistance of the heterogeneous population of cells to the treatment agent.

In some forms, individual cells in the heterogeneous population of cells may be individually monitored and tracked during the step of observation.

In some forms of the method, the step of observation may include monitoring the heterogeneous population of cells during different phases of the cell life cycle.

In some forms of the method, the heterogeneous population of cells may be levitated in a patient sample and it is further contemplated that the patient sample may blood. Of course, blood is only one example, and the patient samples are not contemplated as being limited only to blood.

In some forms of the method, healthy cells may be separated from unhealthy cells. For example, cancer cells may be separated from healthy cells. As another example, red blood cells may be levitated to detect the presence of type I diabetes.

In some forms of the method, during the levitation step, live cells in the heterogeneous population of cells may be separated from dead cells. This separation of live cells from dead cells in the heterogeneous population of cells may used, for example, to determine the efficacy of a treatment agent or to determine the effect of a change in the physical environment on the cells.

In other forms of the method, during the step of separation, different microorganisms may be separated from one another.

In some forms of the method, a characteristic of at least some of the heterogeneous population of cells may be determined by a measured height of the cells in the microcapillary channel. In this way unhealthy cells may be detected without comparison to reference healthy cells.

In a further aspect of the method, the levitation system may include a first mirror on a first open side of the microcapillary channel and a second mirror on a second open side of the microcapillary channel in which the mirrors are oriented at oblique angles relative to the path between the mirrors. While levitating the cells, the method may further include the step of reflecting light from a light source within the microscope with the first mirror through the sample of cells and towards the second mirror to allow for real-time analysis of the cell population. It is also possible for the microscopy device to be an upright fluorescence microscope leveled horizontally on its side, to allow for imaging of the cell population that does not require reflection of light using the mirrors. Additionally, the microscopy device might be a side-viewing microscope, a cell phone camera, a lensless charged-coupled device (CCD) or complementary metal-oxide semiconductor (CMOS) system, or an inverted microscope In accordance with another aspect of the invention, a method for real-time interrogation of cells is provided. The method includes loading a sample of the heterogeneous population of cells into a microcapillary channel containing a magnetically-responsive medium, placing the microcapillary channel containing the sample of cells and the magnetically-responsive medium into a levitation system, levitating the heterogeneous population of cells in the magnetically-responsive medium, and altering magnetic properties of the magnetically-responsive medium. Again, the levitation system used is made up of a set of two magnets producing a magnetic field, with a space between the two magnets that is sized to receive the microcapillary channel. Additionally, the system includes a microscopy device that has a stage between the set of two magnets on which the microcapillary channel is placed. Levitation of the cells occurs by balancing a magnetic force applied to each of the cells by the magnetic field of the magnets with a corrected gravitational force of the cells in the magnetically-responsive medium, which consequently separates the heterogeneous population of cells.

As described previously, it is possible that the heterogeneous population of cells may be selected from that of red blood cells, leukocytes, lymphocytes, phagocytes, platelets, cancer cells, and the like. It is also possible for the magnetically-responsive medium to be a paramagnetic medium and to comprise gadolinium or to be gadolinium based, where the medium can be pure gadolinium, or allow for additional constituents. In a further possibility, locally altering magnetic properties of the magnetically-responsive medium may be accomplished by exposing the magnetically-responsive medium to a low intensity laser beam.

In some forms, the individual cells within the heterogeneous population of cells may be differentiated from others based on at least one of their magnetic susceptibility and cell density created by a cell variant. The variant can be caused by multiple differences between the cells such as cell type, cell-cycle stage, malignancy, disease state, activation state, cellular age, infection state, cellular differentiation, apoptosis of the cell, and phagocytosis of the cell.

Furthermore, it is possible that separation of the individual cells occurs to an equilibrium exhibiting a balance between gravitational forces and magnetic forces on the individual cells.

Furthermore, the separation of the population of cells may be performed at a point of care, as the levitation system being used does not interfere with mobile devices that can be used for remote diagnostics.

In some forms, the levitation system may further include a first mirror on a first open side of the micro capillary channel and a second mirror on a second open side of the microcapillary channel in which the mirrors are oriented at oblique angles relative to the path between the mirrors. While levitating the cells, the method may further include the step of reflecting light from a light source within the microscope with the first mirror though the sample of cells and towards the second mirror to allow for real-time analysis of the cell population. In some forms, the microscopy device may be an upright fluorescence microscope leveled horizontally on its side, to allow for imaging of the cell population in way that that does not require reflection of light using the mirrors. In other forms, the microscopy device might be a side-viewing microscope, a cell phone camera, a lensless charged-coupled device (CCD) or complementary metal-oxide semiconductor (CMOS) system, or an inverted microscope.

Again, the magnets might take a number of different forms. For example, the magnets could be a pair of permanent magnets in an anti-Helmholtz configuration. As another example, the magnets may be electrical magnets. By applying an alternating current to the electrical magnets, the magnetic field gradient may be created.

In some forms of the method, the method may further include the step of observing the heterogeneous population of cells in real time using the microscopy device and the microscopy device may provide various images of the heterogeneous population of cells over a duration of time.

Over this duration of time, further steps may be performed. For example, a physical environment of the heterogeneous population of cells may be altered and a response of the heterogeneous population of cells as a result of the physical environment may be observed. As another example, a treatment agent (such as for example, a drug or an antibiotic) may be introduced into the heterogeneous population of cells and a response of the heterogeneous population of cells as a result of the introduction of treatment agent may be observed. If a treatment agent is introduced, then the method can further include monitoring a continued response of the heterogeneous population of cells to establish the emergence of resistance of the heterogeneous population of cells to the treatment agent.

In some forms, individual cells in the heterogeneous population of cells may be individually monitored and tracked during the step of observation.

In some forms of the method, the step of observation may include monitoring the heterogeneous population of cells during different phases of the cell life cycle.

In some forms of the method, the heterogeneous population of cells may be levitated in a patient sample and it is further contemplated that the patient sample may blood. Of course, blood is only one example, and the patient samples are not contemplated as being limited only to blood.

In some forms of the method, healthy cells may be separated from unhealthy cells. For example, cancer cells may be separated from healthy cells. As another example, red blood cells may be levitated to detect the presence of type I diabetes.

In some forms of the method, during the levitation step, live cells in the heterogeneous population of cells may be separated from dead cells. This separation of live cells from dead cells in the heterogeneous population of cells may used, for example, to determine the efficacy of a treatment agent or to determine the effect of a change in the physical environment on the cells.

In other forms of the method, during the step of separation, different microorganisms may be separated from one another.

In some forms of the method, a characteristic of at least some of the heterogeneous population of cells may be determined by a measured height of the cells in the microcapillary channel. In this way unhealthy cells may be detected without comparison to reference healthy cells.

In accordance with yet another aspect of the invention, a levitation system for separating a heterogeneous population of cells is taught. The system includes a set of two magnets producing a magnetic field, with a space between the two magnets which is sized to receive a microcapillary channel adapted to receive the heterogeneous population of cells, and a microscopy device with a stage between the set of two magnets on which the microcapillary channel is placed.

Furthermore, the system may include a first mirror on a first open side of the microcapillary channel and a second mirror on a second open side of the microcapillary channel in which the mirrors are oriented at oblique angles relative to the path between the mirrors. It is contemplated that, in some forms, the microscopy device may be an upright fluorescence microscope leveled horizontally on its side. In other forms, the microscopy device may be for, example, a side-viewing microscope, a cell phone camera, a lensless charged-coupled device (CCD) or complementary metal-oxide semiconductor (CMOS) system, or an inverted microscope and so forth.

Again, the magnets in the system might take a number of different forms or configurations. For example, the magnets could be a pair of permanent magnets in an anti-Helmholtz configuration. As another example, the magnets may be electrical magnets. By applying an alternating current to the electrical magnets, the magnetic field gradient may be created.

These and still other advantages of the invention will be apparent from the detailed description and drawings. What follows is merely a description of a preferred embodiment of the present invention. To assess the full scope of the invention, the claims should be looked to as the preferred embodiment is not intended to be the only embodiment within the scope of the claims.

BRIEF DESCRIPTION OF THE DRAWINGS

FIG. 1a is a schematic of magnetic cellular levitation and manipulation in a magnetic field. FIG. 1b is a schematic of the forces on a cell due to differences in magnetic susceptibility of the cell and the medium. FIG. 1c is a plurality of views of the magnetic levitation system. FIG. 1d is a front and side contour plot of the magnetic field gradient induced by anti-Helmholtz configured magnets. FIG. 1e is a cell culture image of RBCS in 40 mM $Gd^+$ solution.

FIG. 2a is a density histogram of monocytes, lymphocytes, basophils, PMNs, eosinophils, and RBCs. FIG. 2b is a cell culture image of fluorescently-labeled RBCs, PMNs, and lymphocytes that have undergone magnetically-driven, density based separation in 30 mM Gd+. FIG. 2c is a cell culture image of RBCs levitated in 20, 35, 50, and 100 mM Gd+. FIG. 2d is a cell culture time-lapse image set of the separation of old and young RBCs. FIG. 2e is a fluorescently labeled cell culture image of old and young RBCs at their equilibrium levitation height. FIG. 2f is a graphical representation of the analytical equilibrium time as a function of equilibrium height of old and young RBCs. FIG. 2g is a cell culture time-lapse image set of the levitation of sedimented RBCs in the magnetic levitation device. FIG. 2h is a graphical representation of the time-dependent location of RBCs levitating from the bottom surface of the microcapillary to their equilibrium point.

FIG. 3a is a fluorescently labeled cell culture image detailing the changes in PMN density associated with PMA activation. FIG. 3b is a low magnification image of levitating activated and resting PMN, with an inset showing the shape and optical density differences. FIG. 3c is a pictorial representation of the roundness differences between resting and activated PMN. FIG. 3d is fluorescently-activated sell seeding results for resting and activated PMN. FIG. 3e is a cell culture image detailing the differences in confinement height between resting, activated, and GSH-treated PMNs. FIG. 3f is a cell culture image of magnetically-driven density separation of blood cells. The left panel shows PMNs, lymphocytes, and platelets. The right panel shows resting PMNs, an activated PMN (arrow), and two eosinophils (arrowheads). FIG. 3g is a cell culture image 2 hours after levitation detailing the homo-typical aggregation of PMNs. FIG. 3h is a cell culture image detailing the phagocytosis of *salmonella* by human PMNs.

FIG. 4a shows manipulation of a cell or discrete group of cells via localized laser irradiation. FIG. 4b is a cell culture image set showing an increase in confinement height with UV stimulation, and parmagnetic-mediated cell clustering (dashed circle.) FIG. 4c is a cell culture image set showing the changes in magnetic properties of RBCs due to increased intracellular ATP, causing cell clustering and decreased levitation.

FIG. 5a shows the bright-field image of the levitation of breast cancer cells (TC), PMNs, and lymphocytes from diluted blood spiked with TC. FIG. 5b is the fluorescent imaging of the levitated cells, TC being the larger cells in the top row. FIG. 5c is a merge of FIGS. 5a and 5b. FIG. 5d is a cell culture image of the levitation of healthy RBCs in the presence of 10 mM Na metabisulfate. FIG. 5e is a cell culture image of the levitation of sickle cell RBCs in the presence of 10 mM Na metabisulfate.

FIG. 6a is an annotated photograph of the levitation system. FIG. 6b illustrates the dimensions of some of the supporting elements.

FIG. 10a is a micrograph of fluorescently-labeled breast cancer cells (MDA) spiked in a blood. FIG. 10b shows the separation efficiency of breast cancer cells spiked in a blood sample with different concentrations in which the data points represent the mean of three replicates with ±error bars standard deviation.

FIG. 12a shows micrographs of control (untreated) and HCl-treated MDA breast cancer cells in which the control cells maintain their levitation height (i.e., density), but the HCl-applied cells sink to the bottom of the channel (i.e., z=−500 μm). FIG. 12b details the real-time observation of a HCl-applied single cell in which a viability assay was also conducted using Calcein (green fluorescent) for live cell and Propidium Iodine (red fluorescent) for dead cell. Fluorescent images and bright field images were overlapped each other to compose the micrographs at different time point. While the cell is sinking through the channel bottom and it is gaining density, the fluorescent profile on the cell is changing from green to red indicating a dying cell. FIG. 12c shows real-time density measurement of acid-treated single cells in which it is illustrated that, even if the acid is applied to the cells at the same time, each of the cells behave differently due to cellular heterogeneity.

FIG. 14a graphs the viability of yeast cells after different drug treatment for 24 hours. FIG. 14b illustrates how the levitation heights, magnetic properties and intrinsic magnetic signatures of yeast cells are altered after drug treatment with 100 μM cantharidin and 100 μM fluconazole.

FIG. 15a shows optical density (OD) profiles, FIG. 15b shows distribution inside the channel, FIG. 15c shows calculated single-cell densities, and FIG. 15d provides various micrographs of cells treated with different concentration of drug (Fluconazole), the treatment concentration being listed above each micrograph. It is observed that cellular magnetic profiles and densities change after treatment with different drug concentrations and these changes can be monitored with the magnetic levitation system at the single-cell level.

DETAILED DESCRIPTION OF THE INVENTION

Figure 1:
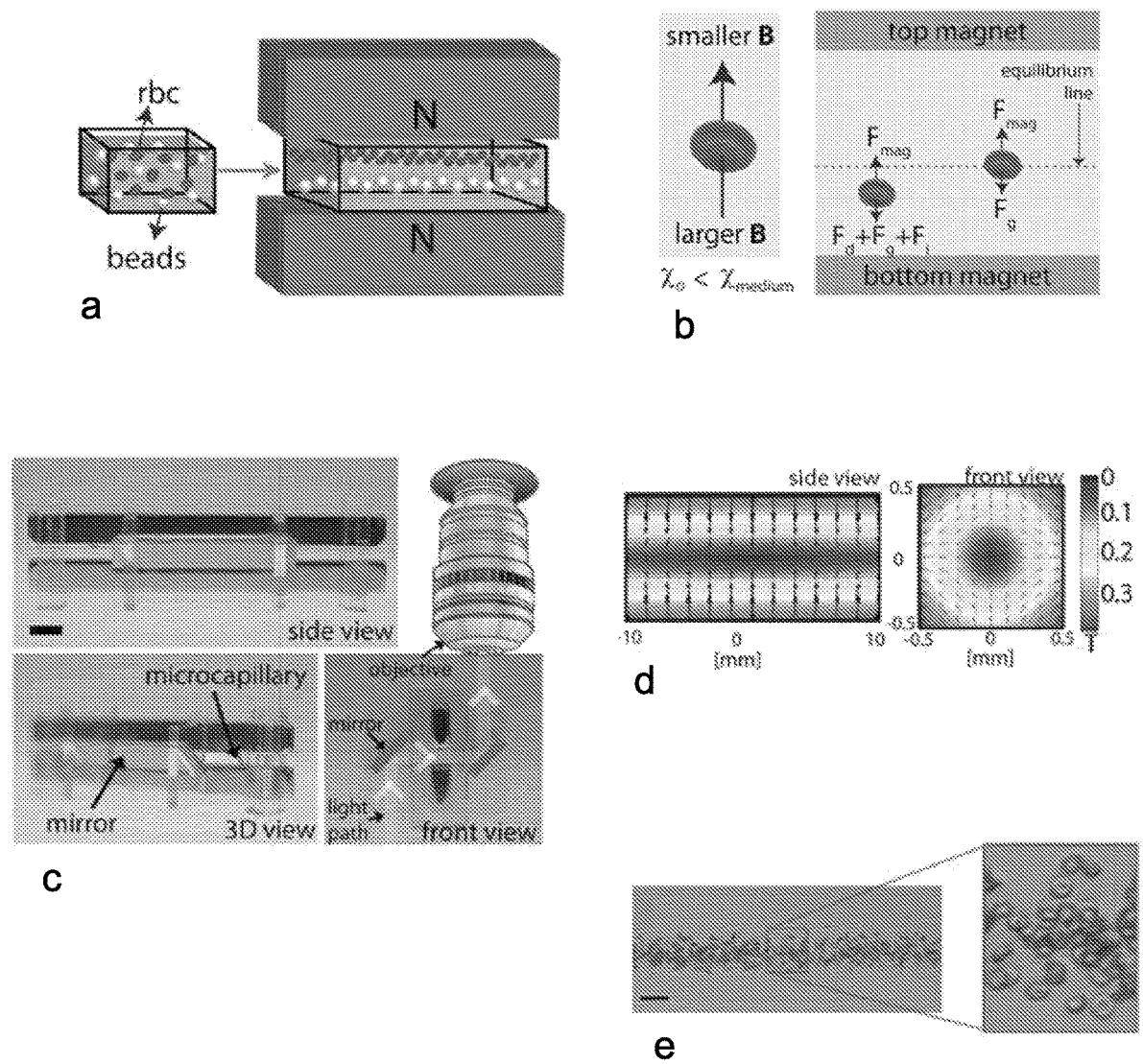
FIG. 1 details magnetic levitation-mediated screening and modulation of cells.

The present disclosure provides a technique for real-time interrogation and monitoring of biological functions of magnetically-suspended cells. To achieve this, heterogeneous populations of cells are levitated and confined in a microcapillary channel, for example a tube, placed between two magnets, for example a pair of permanent magnets in anti-Helmholtz configuration. This enables equilibration of cells at different heights based on the balance between magnetic and corrected gravitational forces acting on cells.

Permanent magnets in the setup can make this system easier to be replicated and used by biomedical labs who would have interest in its broad applications. Using the permanent magnet system, constant magnetic field lines are created and thus, a minimum magnetic field strength location which is spatially constant and dictates the levitation heights of cells. By using alternating current, the magnetic field can be changed in direction and intensity, as well as minimum field strength location. Alternating magnetic field in principle may add new capabilities such as changing levitation height of cells over the time.

Using this approach, red blood cells, leukocytes, platelets and circulating metastatic breast cancer cells, as well as red blood cells of different ages are separated. In addition, cellular processes such as neutrophil activation, phagocytosis, and responses of healthy and sickle red blood cells to dehydration are monitored in real-time. This technique provides a broadly applicable tool for high resolution, real-time cell biology research, as well as disease screening and diagnostics for point-of-care settings.

The core principle of the present magnetic levitation-based method relies on the equilibrium of two opposing forces: the corrected gravitational force and the magnetic force. What is presented is a powerful magnetic levitation-based microfluidic platform, which allows real-time, label-free, high resolution monitoring of cell populations, and is fully compatible with upright or inverted microscopes. This technology offers rapid separation of different cell populations based on their magnetic signatures and densities without the use of antibody-tagged magnetic beads, centrifugation or the use of a specialized, continuous or discontinuous density gradient media. The levitation platform enables unique monitoring functional responses of individual cells to a variety of stimuli, over time, and on a cell-by-cell basis. This approach allows us for the ex vivo investigation of the biological responses following specific, cell-cell and cell-molecule interactions in quasi-physiological, blood stream-like settings.

The underlying mechanisms for levitation of cells in a microcapillary can be understood as follows. Under an applied magnetic field, B, created by the two magnets placed in anti-Helmholtz configuration (same poles facing each other), magnetic force, $F_m$, exerted on a cell is given in Equation 1. Corrected gravitational force, $F_g$, acting on a cell is given in Equation 2

$$F_m = \left(\frac{\chi_{cell} - \chi_m}{\mu_0}\right)V(B \cdot \nabla)B \quad (1)$$

$$F_g = (\rho_{cell} - \rho_m)Vg \quad (2)$$

Here, $\mu_0 = 4\pi \times 10^{-7}$ (N·A$^{-2}$) is the magnetic permeability of free space, $\rho_m$ (kg·m$^{-3}$) is the density of the paramagnetic medium, $\chi_m$ is the non-dimensional magnetic susceptibility of the paramagnetic medium, $\rho_{cell}$ (kg·m$^{-3}$) is the density of the cell, $\chi_{cell}$ is the non-dimensional magnetic susceptibility of the suspended cell, V (m$^3$) is the volume of the cell, and g is the vector of gravity. The cell is assumed to have a homogeneous distribution of density and magnetic susceptibility throughout its volume.

The magnetic force, $F_m$, depends on the position of cell (as the magnetic field spatially changes within the microcapillary) and is directed towards the minimum of the magnetic field. The corrected gravitational force, $F_g$, does not depend on the location of the cell inside the microcapillary. The Stoke's drag force, $F_d$ is given by equation 5 for a spherical particle of radius, R, and volume, $V=4\pi R^3/3$.

In a transient case, for example before cell reaches equilibrium point where the magnetic force balances with the corrected gravity force, inertial forces, for example the term at the left in Equation 3, and drag force, $F_d$, which depends on the migration velocity of cell, equation 5, will be active as described in equation 3. At equilibrium, the drag and inertial forces vanish, and the magnetic and gravitational forces acting on the cell will balance each other, as given in Equation 4.

$$ma = F_m + F_g + F_d \quad (3)$$

$$F_g + F_m = (\rho_{cell} - \rho_m)Vg + \left(\frac{\chi_{cell} - \chi_m}{\mu_0}\right)V(B \cdot \nabla)B = 0 \quad (4)$$

$$F_d = 6\pi\eta R v \quad (5)$$

$$F_g = (\rho_{cell} - \rho_m)Vg = \begin{pmatrix} 0 \\ 0 \\ -(\rho_{cell} - \rho_m)Vg \end{pmatrix} \quad (6)$$

$$F_m = \left(\frac{\chi_{cell} - \chi_m}{\mu_0}\right)V(B \cdot \nabla)B = \quad (7)$$

$$\begin{pmatrix} \left(\frac{\chi_{cell} - \chi_m}{\mu_0}\right)V\left(B_x\frac{\partial B_x}{\partial x} + B_y\frac{\partial B_x}{\partial y} + B_z\frac{\partial B_x}{\partial z}\right) \\ \left(\frac{\chi_{cell} - \chi_m}{\mu_0}\right)V\left(B_x\frac{\partial B_y}{\partial x} + B_y\frac{\partial B_y}{\partial y} + B_z\frac{\partial B_y}{\partial z}\right) \\ \left(\frac{\chi_{cell} - \chi_m}{\mu_0}\right)V\left(B_x\frac{\partial B_z}{\partial x} + B_y\frac{\partial B_z}{\partial y} + B_z\frac{\partial B_z}{\partial z}\right) \end{pmatrix}$$

Here, v is the velocity of the particle (m/s) and $\eta$ is the dynamic viscosity of the suspending medium (kg/ms). In the z-axis, where the corrected gravitational force is aligned, the balance of forces can be written as, $$(\rho_{cell} - \rho_m)Vg + \left(\frac{\chi_{cell} - \chi_m}{\mu_0}\right)V\left(B_x\frac{\partial B_z}{\partial x} + B_y\frac{\partial B_z}{\partial y} + B_z\frac{\partial B_z}{\partial z}\right) = 0 \quad (8)$$

Here, it is assumed that the absolute value of the third term $$\left(B_z\frac{\partial B_z}{\partial z}\right)$$

in Equation 8 is larger than the absolute value of the sum of the first and second terms $$\left(B_x\frac{\partial B_z}{\partial x} + B_y\frac{\partial B_z}{\partial y}\right),$$

and a linear change of $B_z$ with respect to z-axis, therefore $$B_z \frac{\partial B_z}{\partial z} \gg \left( B_x \frac{\partial B_z}{\partial x} + B_y \frac{\partial B_z}{\partial y} \right) \quad (9)$$

$$B \equiv \begin{pmatrix} B_x \\ B_y \\ B_z \end{pmatrix} = \begin{pmatrix} 0 \\ 0 \\ -\frac{2B_0}{d}z + B_0 \end{pmatrix} \quad (10)$$

Equation 8 can be solved after substituting B, given by Equation 10, into Equation 8 to find the equilibrium height, h, as seen in Equation 11. Equilibrium height, h, is the vertical distance where the magnetic force and the corrected gravitational force cancel each other. From equation 11, $\rho_{cell}$ can be extracted as well and written as a function of h, Equation 12a, with the coefficients $\alpha$ and $\beta$, Equation 12b&c.

$$h = \frac{(\rho_{cell} - \rho_m)g\mu_0 d^2}{(\chi_{cell} - \chi_m)4B_0^2} + \frac{d}{2} \quad (11)$$

$$\rho_{cell} = \alpha h + \beta \quad (12a)$$

$$\alpha = \frac{4(\chi_{cell} - \chi_m)B_0^2}{g\mu_0 d^2} \quad (12b)$$

$$\beta = \rho_m - \frac{2(\chi_{cell} - \chi_m)B_0^2}{g\mu_0 d} \quad (12c)$$

Figure 7:
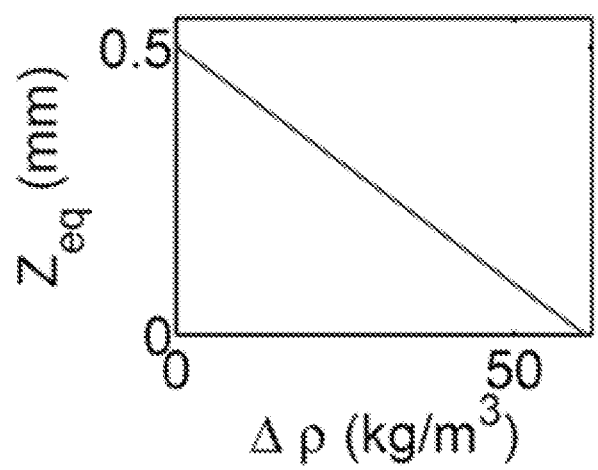
FIG. 7 is a graphical representation of the equilibrium height as a function of density difference between the suspending cell and the paramagnetic medium.

Equilibrium height as a function of density difference between cell and the suspending liquid is plotted in FIG. 7.

The time to equilibrium can also be calculated. Here, it is defined that equilibrium time, $t_0$, is the time that elapses while a cell moves from its initial location, $z_i$ (for example, the bottom of the microcapillary), to another position, $z_f$ (for example the levitation height), in the microcapillary. To find $t_0$, here it can be assumed in Equation 3 that the cell has zero acceleration (a=0) and is moving with its terminal velocity, as described by Equation 13.

$$0 = F_m + F_g + F_d \quad (13)$$

The z component of equation 13 was found by substituting Equations 5, 8, and 10 into Equation 13, the substitution shown as Equation 14a. After integrating Equation 14a, the time that elapses while a cell reaches equilibrium was found as described by Equation 15. While the cell gets closer to the equilibrium point, the driving magnetic force becomes smaller and thus, the velocity of the cell becomes smaller, which in turn decreases the drag force. In the mathematical model, the cell never reaches equilibrium, therefore $t_0 = \infty$ when the Equation 15 is solved for $z_f = h$.

$$\frac{dz}{dt} = \xi z + \zeta \quad (14a)$$

$$\xi = \frac{8}{9} \frac{R_{eq}^2 B_0^2}{\mu_0 d^2 \eta}(\chi_{cell} - \chi_m) \quad (14b)$$

$$\zeta = -\frac{2}{9} \frac{R_{eq}^2}{\eta}\left( (\rho_{cell} - \rho_m)g + \frac{2B_0^2}{\mu_0 d}(\chi_{cell} - \chi_m) \right) \quad (14c)$$

$$t_0 = \frac{1}{\xi}\ln\left(\frac{\xi z_f + \zeta}{\xi z_i + \zeta}\right) \quad (15)$$

Figure 2:
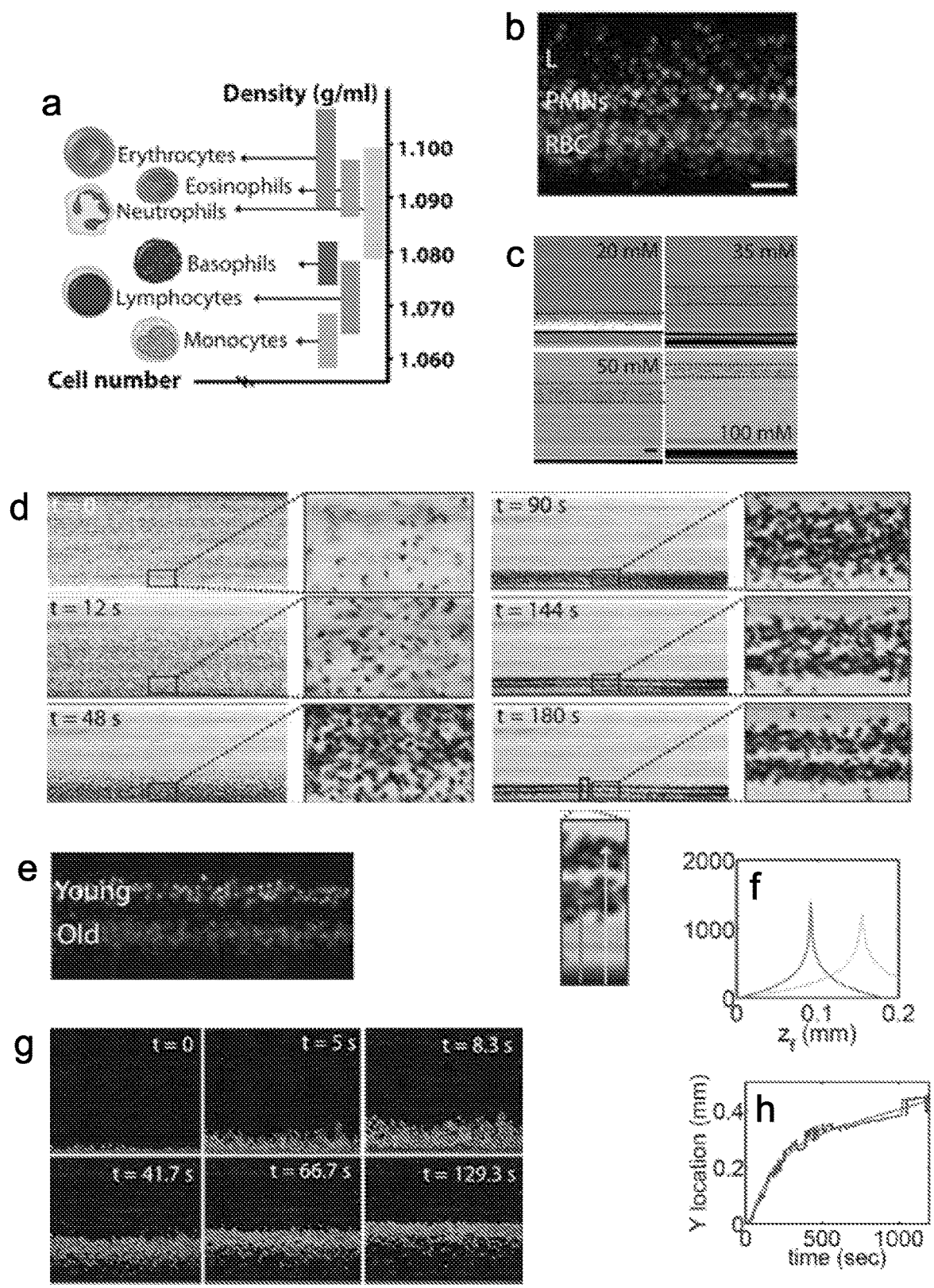
FIG. 2 details the characterization of cell separation using magnetic levitation.

Equilibration times of new and mature red blood cells are plotted as a function of equilibrium height in FIG. 2h. In some experiments, the magnetic susceptibility of cell or the ambient paramagnetic fluid was altered by exposing it to UV and causing the formation of reactive oxygen species (ROS).

EXAMPLES

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1: Magnetic Levitation Approach and Underlying Mechanisms

Negative differences between the magnetic susceptibilities of suspending objects, $\chi_o$, (for example, a heterogeneous group of cells) and suspending medium ($\chi_{medium}$) create a magnetic force field causing objects to be confined at different heights depending on the balance between corrected gravitational forces and magnetic forces as depicted in FIG. 1a. Negative difference between the magnetic susceptibilities of an object ($\chi_o$) and suspending medium ($\chi_{medium}$) causes the object to move away from larger magnetic field strength site to lower magnetic field strength. Until an object, for example, a red blood cell (RBC) suspended in a paramagnetic medium reaches the equilibrium height, a set of forces, such as fluidic drag, inertial, gravitational, and magnetic forces, continuously act on the object. As the object approaches equilibrium, its velocity, and thus drag and inertial forces become progressively smaller, which can be seen in FIG. 1b.

Figure 6:
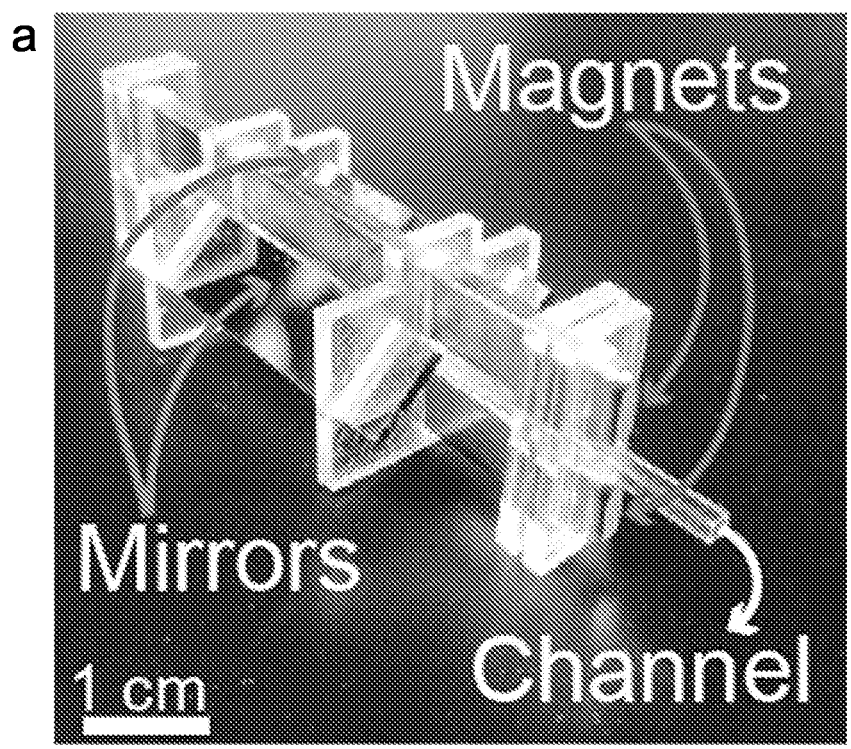
FIG. 6 is a schematic of one embodiment of the levitation system.
Figure 6:
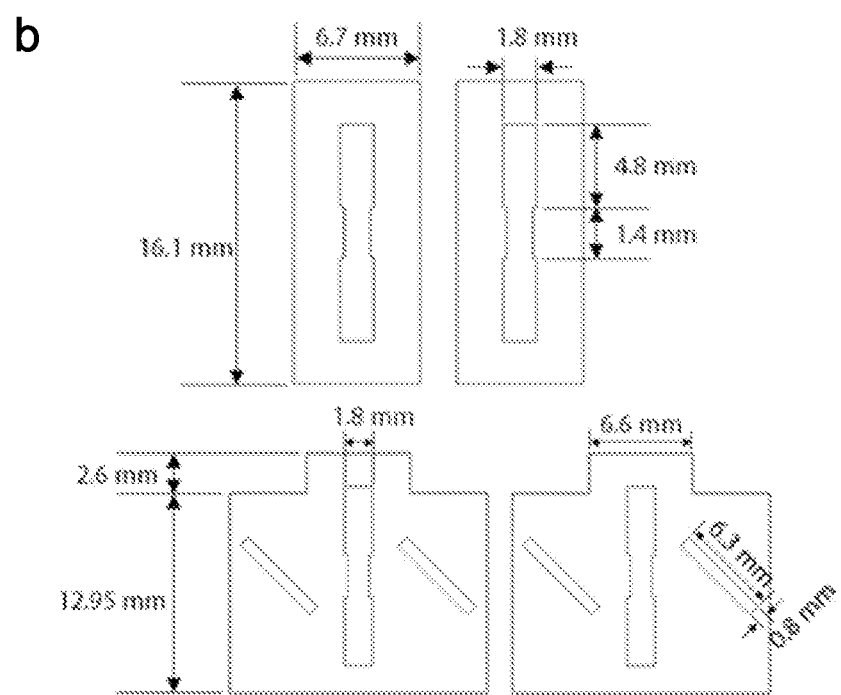

In this setup and with additional forward reference to the device illustrated in FIGS. 6a and 6b, a micro capillary tube that is 50 mm long with a 1 mm×1 mm square cross-section is placed between two permanent N52 grade neodymium magnets (NdFeB, 50 mm length, 2 mm width, and 5 mm height) in an anti-Helmholtz configuration (same poles facing each other). These parts were assembled together using 1.5-mm-thick polymethyl methacrylate (PMMA) pieces that were cut with a laser system (VLS 2.30 Versa Laser). Before each separate measurement, the microcapillary channel was plasma treated for 2 minutes at 100 W, 0.5 Torr (IoN 3 Tepla) and then placed between the magnets. Two mirrors are placed at 45° (or other oblique angles) to image levitation heights using an inverted microscope (Zeiss Axio Observer Z1) under a 5× objective or 20× objective, to create a device compatible with conventional microscopy systems for high resolution spatiotemporal monitoring of cells during levitation, which is detailed in FIG. 1c. Due to the particular placement of the two magnets, with the symmetric magnetic field strength distribution with respect to each axis (FIG. 1d), the suspended cells levitate at a position that depends on both the location of minimum field strength and the ratios of the magnetic susceptibility and cellular density.

To test this setup, RBCs that have been isolated from a healthy donor are suspended in 40 mM gadolinium-based (Gd+) paramagnetic medium. The paramagnetic solution used for all experiments presented here is currently employed for MRI investigations in humans, is non-toxic, and compatible with human blood cells. Following 10 minutes of magnetic confinement, RBCs stably levitated at a height of approximately 300 μm from the bottom magnet, forming a small, wall-less, blood stream-like assembly as seen in FIG. 1e.

For higher resolution brightfield and fluorescence imaging of (20×, 40× and 60×), a mirror-free setup coupled to a fluorescence upright microscope leveled on its side is used.

Example 2: Cell Separation by Magnetic Levitation

Mass density distribution of human blood cells varies between 1.055 and 1.11 g/mL as illustrated FIG. 2a. Volumetric mass density, defined as mass per unit volume, is one of the most fundamental physical parameters that characterize a cell. Several cellular events such as differentiation, cell death (apoptosis/necrosis), malignancy, phagocytosis, and cell-age cause permanent or transient changes in cell volumetric mass density.

The cell-separation capability of the setup was assessed by magnetically confining isolated and fluorescently labeled RBCs, polymorphonuclear leukocytes (PMNs), and lymphocytes, as shown in FIG. 2b.

To isolate PMNs, 40 mL of blood was obtained by venipuncture from healthy adult volunteers in accordance with the guidelines of the Institutional Review Board (IRB) of Beth Israel Deaconess Medical Center, and after informed consent in accordance with the Declaration of Helsinki. The blood was drawn into a 60 mL syringe containing 14 mL 6% Dextran T500 and 6 mL citrate solution. After 1 hour to allow for separation, the buffy coat was obtained and layered on top of 15 ml of FICOLL® (a neutral, highly branched, high-mass, hydrophilic polysaccharide which dissolves readily in aqueous solutions obtained from GE Healthcare) and centrifuged at 350×g for 15 minutes. The pellet, consisting of PMNs, eosinophils and contaminating RBCs, was resuspended in 25 ml of 0.2% NaCl for 45 seconds to lyse RBCs, followed by addition of an equal volume of 1.6% NaCl with continuous end-over-end mixing to balance the salt solution. The suspension was centrifuged at 350×g for 5 minutes, and the pelleted PMNs were washed and resuspended in 1 mL HBSS++.

Results show that cells suspended in 30 mM Gd+ solution form distinct density and cell specific confinement bands populated by RBCs, PMNs and lymphocytes alone.

The effect of magnetic strength of the suspension solution on the focusing height of RBCs was then investigated by progressively increasing the molarity of Gd+ solution used for RBC suspension as can be seen in FIG. 2c. It was found that an increase in the molarity of Gd+, and thus magnetic susceptibility of the suspension media, causes a gradual increase in the focusing height of cells.

RBCs are formed in bone marrow by hematopoietic stem cells (HSCs) and circulate for 100-120 days before they are recycled by tissue macrophages. Circulating RBCs continuously releases microparticles that progressively decrease their surface-to-volume ratio and increase their density.

To investigate if the sensitivity resolution of the setup was precise enough to separate young (1.09 g/mL) from old (1.11 g/mL) RBCs based on their different volumetric mass densities, a mixture of fluorescently labeled young and old RBCs, which were isolated by PERCOLL® gradient (PERCOLL® being colloidal silica particles which have been coated with polyvinylpyrrolidone), was levitated in 30 mM Gd+ solution.

To allow for fluorescent labeling, old and new RBCs were separated. RBCs (10% hematocrit) were collected either by venipuncture or fingerprick and washed 3 times in HBSS++. RBCs were layered on 13 mL of a solution containing 77% PERCOLL® 10% 1.5 M NaCl, and 13% ddH2O, followed by centrifugation at 15000×g for 20 min, with the brake off. New RBCs at the uppermost layer were collected, washed to remove the PERCOLL® solution, and resuspended in 1 mL HBSS++. Similarly, old RBCs that separated to the bottom of the solution were collected, washed and resuspended in 1 mL HBSS++.

RBCs, which were initially in random distribution in the microcapillary, started to focus at different levitation heights when exposed to magnetic field (snapshots of the time lapse recording are shown in FIG. 2d). Fluorescently labeled young and old RBCs at their respective equilibrium levitation heights are shown in FIG. 2e.

Using a time-lapse recording of the levitation process, the specific equilibrium time function of focusing height of old and young RBCs was evaluated analytically as shown in FIG. 2f. Briefly, equilibrium heights were measured from the bottom magnet for young and old RBCs and were found to be 0.156 mm and 0.092 mm, respectively. Density differences between each cell and suspension liquid were calculated using FIG. 7, which was plotted using Equation 11. By substituting density differences into Equations 14 and 15, equilibrium times were plotted, which can be seen in FIG. 2f.

The capability of the setup to levitate gravitationally-sedimented cells was also tested. RBCs were loaded in the glass microcapillary tube, and then placed on the bench for 15 minutes until all cells passively (gravitationally) sedimented along the bottom of the microcapillary. The microcapillary tube was then loaded in the magnetic levitation setup. Due to their relative diamagnetic properties compared to suspension liquid, cells started to move away from the magnet and levitate toward their density-dependent equilibrium point, as shown in FIG. 2g. Finally, the location of cells during magnetic focusing as a function of time using time-lapse microscopy was quantified, as seen in FIG. 2h.

Example 3: Static Levitation of Functionally-Altered Blood Cells

PMNs are phagocytes, cells capable of sensing and responding to microorganism-specific danger signals followed by specific binding and internalization of foreign microorganisms or particles. Phagocytic events result in the formation of reactive oxygen species (ROS) and ROS-mediated activation of hydrolytic enzymes. Generation of ROS and reactive nitrogen species (RNS) will cause changes in the magnetic signature of phagocytes, whereas the dynamic interplay between the endocytic and exocytic processes during phagocytosis would directly impact the volumetric mass density of activated PMNs.

Freshly isolated PMNs were activated by incubating them either with buffer (resting PMN), GSH-ME (GSH-treated PMN), or 10 nM PMA (activated PMN) for 5 minutes, washing twice, mixing, and resuspending them in 35 mM Gd+ solution. Prior to treatments, cells were labeled either with Cell Tracker Green (activated PMN) or Cell Mask Deep Red (GSH-treated PMN).

The response of human PMNs during the activation phase of phagocytosis was studied by incubating PMNs with phorbol 12-myristate 13-acetate (PMA, 10 nM) for 10 minutes. As a control, PMNs were left in buffer for 10 minutes. Cells were then washed, fluorescently labeled, mixed together, and loaded into the magnetic levitation setup. Magnetic focusing revealed distinct differences between control and activated PMNs, both in terms of size, shape, optical density, as well as magnetic and mass density signatures, as shown in FIG. 3a.

Activated PMNs generate intracellular paramagnetic ROS that actively reduces the difference between the magnetic susceptibilities of the cells and suspending medium. As a consequence, activated PMNs would be expected to "sink" compared to buffer-treated ones. However, the results show that the decrease in density promoted by cell activation is more pronounced than the transient increase in magnetic properties and, as a result, the cells levitated to higher elevations than the control.

The morphological differences between activated and normal PMNs were evaluated by measuring the roundness of cells, defined as $$\frac{\text{perimeter}^2}{(4 \cdot \pi \cdot \text{area})}.$$

Figure 3:
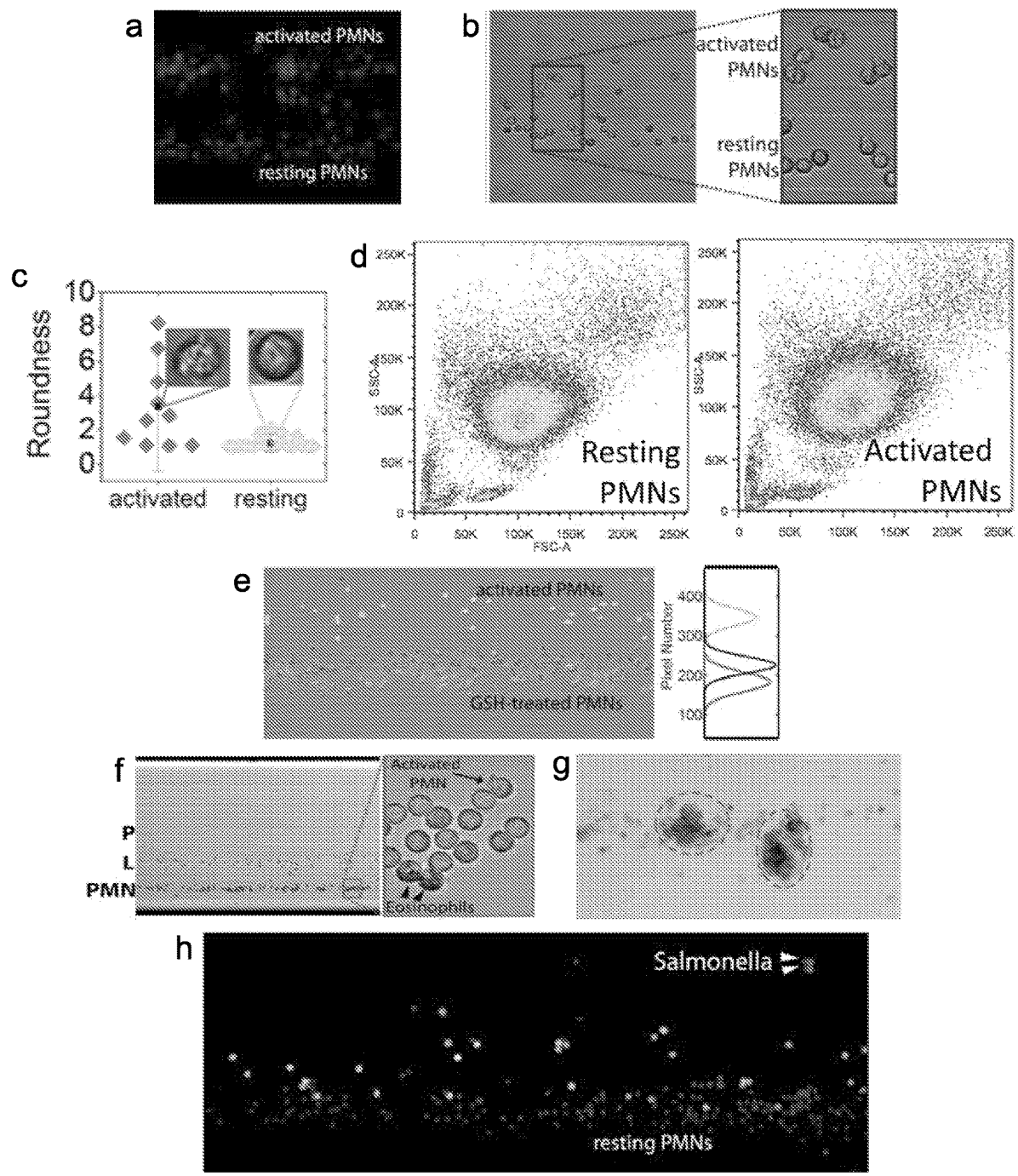
FIG. 3 details the static levitation of functionally-altered blood cells.

The calculated roundness values, shown in FIG. 3c, indicate significant difference between PMA-activated and buffer-treated PMNs. The same samples were simultaneously examined by flow cytometry for changes in forward and side-scatter properties of PMNs associated with PMA activation, shown in FIG. 3d. When compared to flow cytometry, magnetic levitation allows direct visualization of cells, as well as increased shape and size-detection sensitivity and resolution, while simultaneously providing real-time density measurements on a cell-by-cell basis.

To further understand the effect of intracellular ROS on the final position of levitating cells, cell permeable glutathione (GSH), an ROS scavenger was used. Results, depicted in FIG. 3e, show that GSH-treated PMNs equilibrated closer to resting PMNs, whereas activated, low density PMNs were focused as expected, above these two groups.

To test the density resolution of the setup, a mixture of PMNs, lymphocytes, and platelets was levitated. High magnification imaging of the resting PMNs revealed that, while most of the cells were non-activated, a few, indicated by the arrow in FIG. 3f, show early signs of activation, through both shape changes and height positions, indicative of lower cell density. In addition, contaminating eosinophils were positioned at the bottom of the PMN column, consistent with their density being equal to or greater than that of the densest PMNs, as seen in FIG. 2a. Two hours after continuous levitation, as shown in FIG. 3g, PMNs underwent self-activation followed by integrin-mediated homo-typical aggregation.

Of note, some of the PMN clusters also displayed a lower position compared to non-activated PMNs, suggesting that intracellular, paramagnetic ROS species formed during activation also influenced the confinement height of the cells. Next, the density changes during human PMN phagocytosis were studied by incubating freshly isolated PMNs with fluorescently labeled *Salmonella* Montevideo. To allow for PMN phagocytosis, Cell Tracker Green-labeled PMNs ($5 \times 10^5$) were added to microfuge tubes containing 600 µl, of HBSS/0.1% BSA. Serum-opsonized Alexa-594-labeled S. Montevideo ($1 \times 10^6$), was added to the PMNs at a 10:1 ratio, and the mixture was incubated for 10 min at 37° C. with end-over-end rotation at 8 rpm. PMNs were washed, mixed with Hoechst 33342-labeled resting PMNs and resuspended in 35 mM Gd+ solution. The *Salmonella* Montevideo (American Type Culture Collection) used was grown overnight in Bacto nutrient broth (Difco) and quantified (0.5 $OD_{600}=4.5 \times 10^8$ cells/mL). Bacteria were gently pelleted, washed, and resuspended in HBSS.

A cell culture of this study can be seen in FIG. 3h. The results show that phagocytic PMNs have significantly decreased density although there was no clear relationship between the numbers of *Salmonella* ingested, originally shown as red in FIG. 3h (although now not readily apparent due to the grey-scale conversion of the image), and the confinement height of the PMNs.

Example 4: Functional Interrogation of Magnetically-Levitated Blood Cells

The magnetic levitation setup permits acquisition of high resolution images at various points in time followed by investigation of unique responses of individual cells in the population. This provides extensive morphological and functional mapping capabilities over time on a cell-by-cell basis for a given population.

Figure 4:
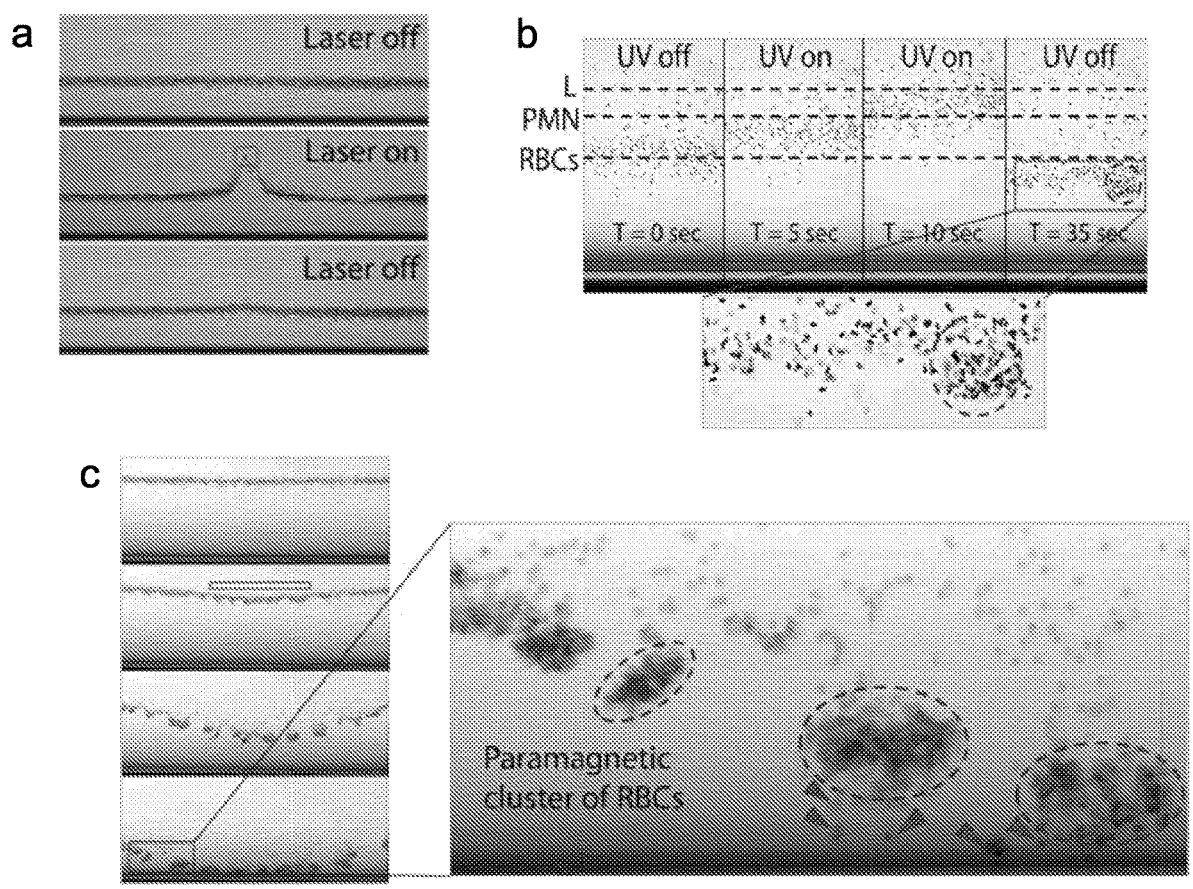
FIG. 4 details the functional interrogation of magnetically-levitated blood cells.

The proposed platform allows for single cell manipulation by exposing a particular area of confined cells to a low intensity laser beam, which allows extensive spatiotemporal height adjustment of the targeted cell or cell group by transiently and locally altering the magnetic properties of the gadolinium solution, which is depicted in FIG. 4a.

One levitation setup was fabricated using 1.5-mm-thick polymethyl methacrylate (PMMA) (McMaster Carr). Setup components were cut to the dimensions given in FIG. 6b (VERSALASER™; Universal Laser Systems Inc.). In this experimental setup, a microcapillary tube (VITRO-TUBES™ Square Capillary Microcells, Borosilicate Glass 8100, Vitrocom, Mountain Glass, N.J.) with 1 mmx1 mm (outer edge, wall thickness 0.2 mm) square cross-section is placed between two permanent neodymium magnets (NdFeB) in an anti-Helmholtz configuration (same poles facing each other). Two gold-coated mirrors are placed at each open side of the microcapillary at 45 degrees to create a device compatible with conventional microscopy systems for high resolution spatiotemporal monitoring of cells during levitation. Microfluidic chips with easily accessible, inexpensive components and magnets have been designed and fabricated, allowing widespread use of this method by other researchers around the world.

In one experiment, following RBC confinement, a square area of 20×20 µm in the middle of stably levitated RBCs was illuminated with a 30 mW, 488 nm laser beam at 0.34% intensity continuously for 1 minute using a Vector Photomanipulation unit (3i). The targeting of the beam was kept on the same cell throughout the experiment.

In another experiment, a larger area (900×900 um) of levitated RBCs, PMNs and lymphocytes was UV-irradiated. For the duration of irradiation, cells progressively increased their levitation heights due to increased magnetic properties of the suspension media. Immediately after UV stimulation was turned off, cells began to return to their original positions, although RBCs equilibrated at a lower height than original, indicating potentially that intracellular, UV-induced ROS increased the paramagnetic signature of RBCs. Cell cultures taken both when UV-irradiation was on and off are depicted in FIG. 4b.

Consistent with this possibility that UV-induced ROS increased the paramagnetic signature of RBCs, in areas with increased cell density, RBCs formed distinct aggregates, shown as the red circle in FIG. 4b, likely due to weak paramagnetic attraction between ROS-containing RBCs. To test this hypothesis, a burst of extracellular ATP to dissociate 2-3 DPG (2,3-diphosphoglycerate) from hemoglobin was used, a process that also transitions RBCs from diamagnetic to weak paramagnetic cells. Isolated RBCs were washed and resuspended in HBSS++ containing 40 mM Gd+ and 10 mM caged ATP (Life Technologies). RBCs were loaded into the capillary, placed between the magnets, and allowed to focus. Next, a region of 60×900 μm located about 70 μm above the levitating RBCs was selected and illuminated by a 488 nm laser beam for 1 second at 100% intensity. The un-caged ATP, released into the suspension increased the extracellular concentration of ATP from 0 to nearly 10 mM. Cells were recorded using Slidebook 5.5.

Following photolysis, caged-ATP became ATP, effectively increasing the concentration of biologically-active, extracellular ATP from 0 to close to 10 mM. The high concentration of extracellular ATP (10 mM) compared to intracellular (about 1-1.3 mM) promoted an abrupt increase in intracellular ATP, followed by dissociation of 2,3 DPG from hemoglobin, and changes in the magnetic properties of RBCs that led to paramagnetic-mediated cell clustering, represented by the circles in FIG. 4*c*, and loss of levitation. As RBCs approached the bottom magnet, represented by the arrows in FIG. 4*c*, the interaction between the paramagnetic RBCs and the magnet increased progressively, eventually overcoming the weak paramagnetic interactions between cluster-forming RBCs, and leading to a gradual dispersal of RBC clusters.

Example 5: Versatility of the Magnetic-Levitation Based Approach for Clinical POC Diagnosis To demonstrate the wide applicability of this magnetic levitation-based approach over different cell types, circulating cancer cells, and sickled RBCs were used. Metastasis is a process responsible for spreading malignant cells from the primary site to another, non-adjacent site. When malignant cells break away from a tumor, they migrate to other areas of the body through the bloodstream or the lymph system, becoming circulating tumor cells (CTC).

The breast cancer cell line MDA-MB-231 being used was purchased from the American Type Culture Collection and cultured in DMEM supplemented with 10% FBS, 100 units/mL penicillin, and 100 μg/mL streptomycin and maintained at 37° C. under 5% $CO_2$.

A heterogeneous group of cells by spiking normal blood with breast cancer cells (CTC) pre-stained with the cell permeable, DNA-specific dye Hoechst 33342 was prepared. The cell mixture was then magnetically focused for 15 minutes in a 20 mM Gd+ solution that allowed levitation only of PMNs and lymphocytes, but not that of RBCs. CTCs were readily identified, shown as the cells with blue nuclei in FIG. 5*a*, in the top row, from the multi-cell suspension being confined close to the center of the microcapillary tube, tens to hundreds of micrometers away from lymphocytes and PMNs respectively.

Figure 5:
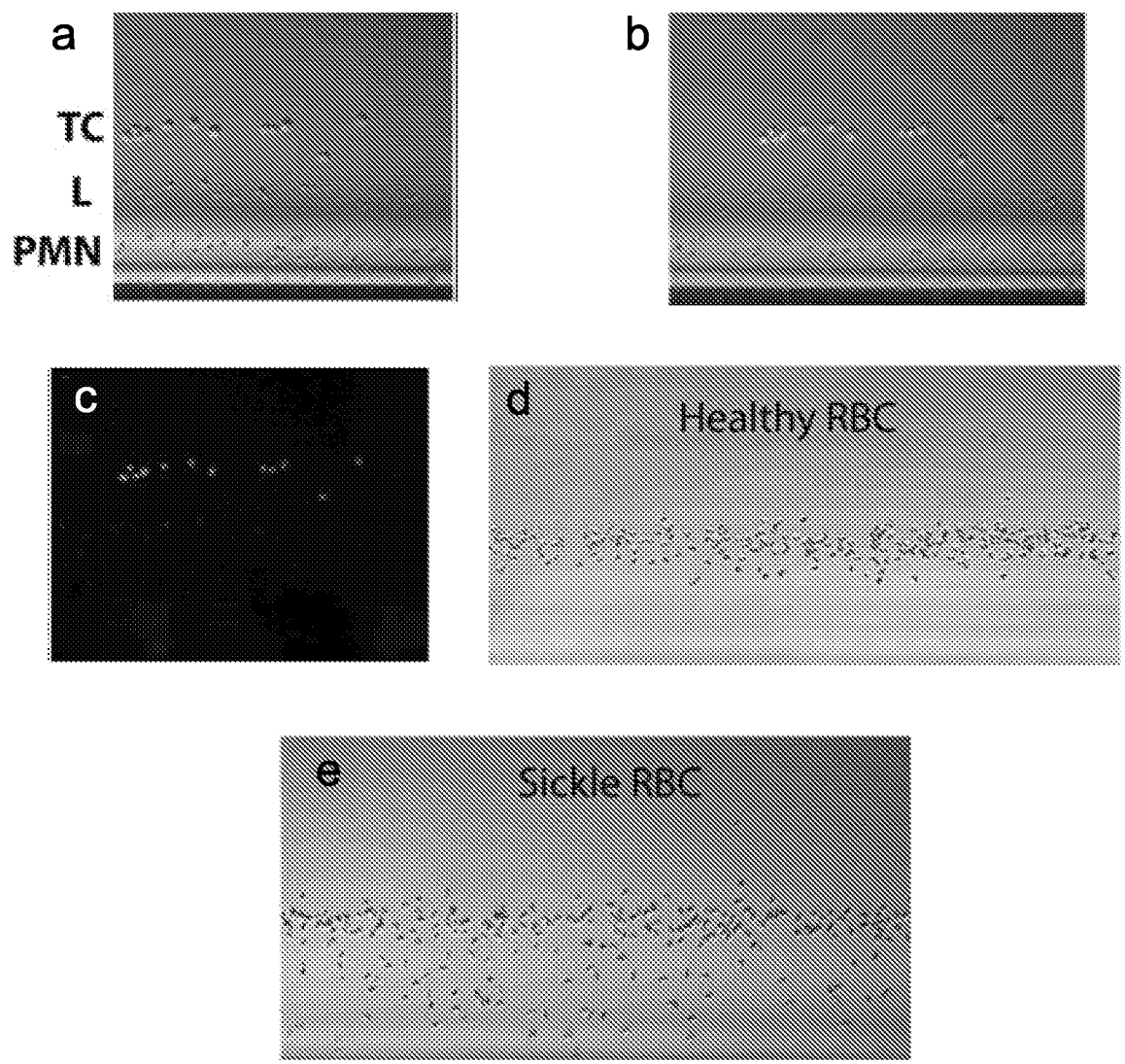
FIG. 5 details the versatility of magnetic levitation for clinical point of care diagnosis.

Additionally, it is shown that RBCs isolated from a healthy donor and a patient homozygous (SS) for sickle cell disease can be separated rapidly and specifically based on their individual responses to 10 mM sodium metabisulfite-induced dehydration, as can be seen in FIG. 5*c*.

RBCs isolated from healthy and sickle cell disease patients were washed three times and incubated with 10 μM sodium metabisulfite for 10 minutes at room temperature. Cells were levitated as described above and images were recorded after 10 minutes. To increase the contrast of the cells against the background, images were filtered using an edge detection algorithm (Roberts). This treatment renders a subpopulation of sickle RBCs, likely younger RBCs, significantly denser than healthy RBCs.

Example 6: Label Free Detection of Circulating Tumor Cells (CTCs) and Circulating Tumor Microemboli (CTM)

With reference to FIGS. 8-11, label free detection of circulating tumor cells (CTCs) and circulating tumor microemboli (CTM) are illustrated.

Figure 8:
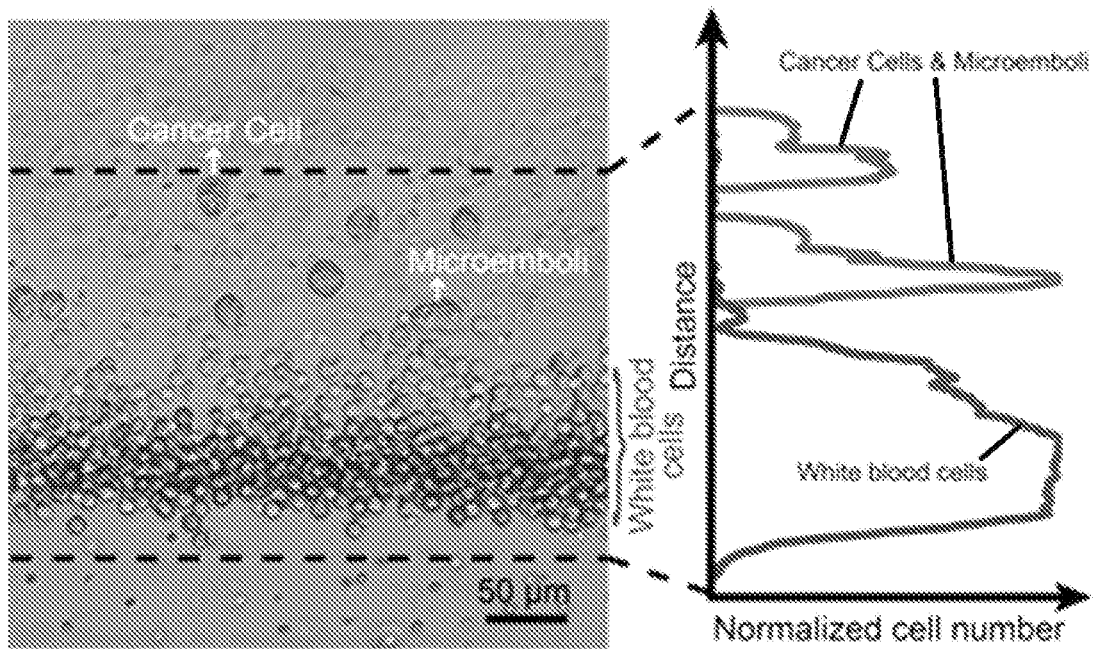
FIG. 8 is a micrograph of blood cells spiked with non-small cell lung cancer (NSCLC) cells (HCC-827) and the corresponding observed cell distribution profile. For this experiment, RBCs were previously lysed and cells were sorted using 30-mM Gadavist (Gd+) solution.

With reference being made to FIG. 8, CTCs and CTM of non small cell lung cancer (NSCLC) were identified using the magnetic levitation system, where these cancer cells were levitated higher than the blood cell population as illustrated in the left panel. In the right panel, a corresponding profile is illustrated which identifies the normalized cell number at particular distances (i.e., levitational heights). From the labeled peaks, it can be seen that the cancel cells and microemboli separate upwardly from the white blood cells, which remain in at a comparatively lower height.

Figure 9:
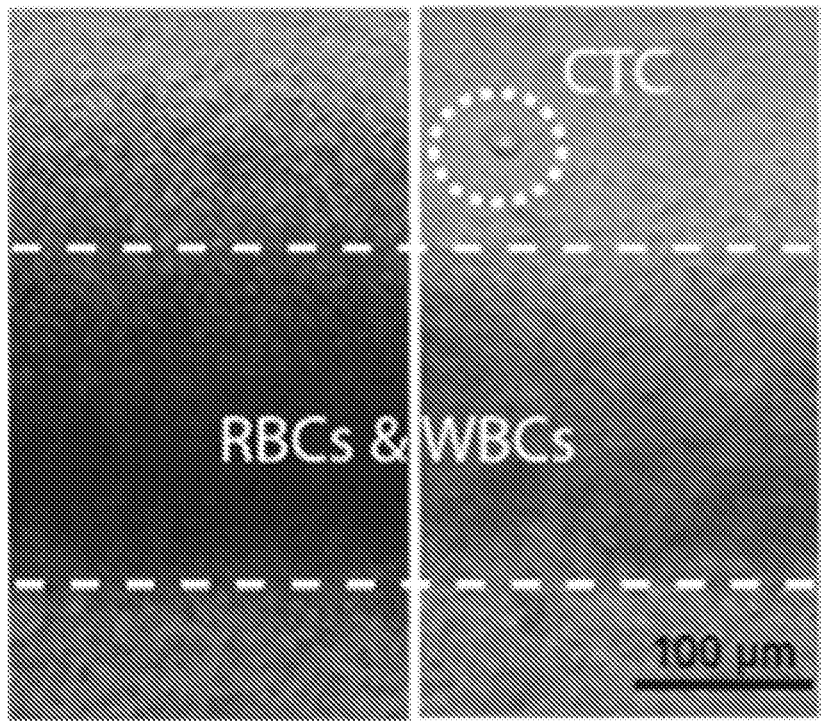
FIG. 9 is a micrograph of a non-small cell lung cancer cell (NSCLC) detected from a patient blood sample.

Turning now to FIG. 9, CTCs were also monitored also in NSCLC patient blood sample with the magnetic levitation system. The dotted white circle indicates a CTC in the patient blood sample.

Figure 10:
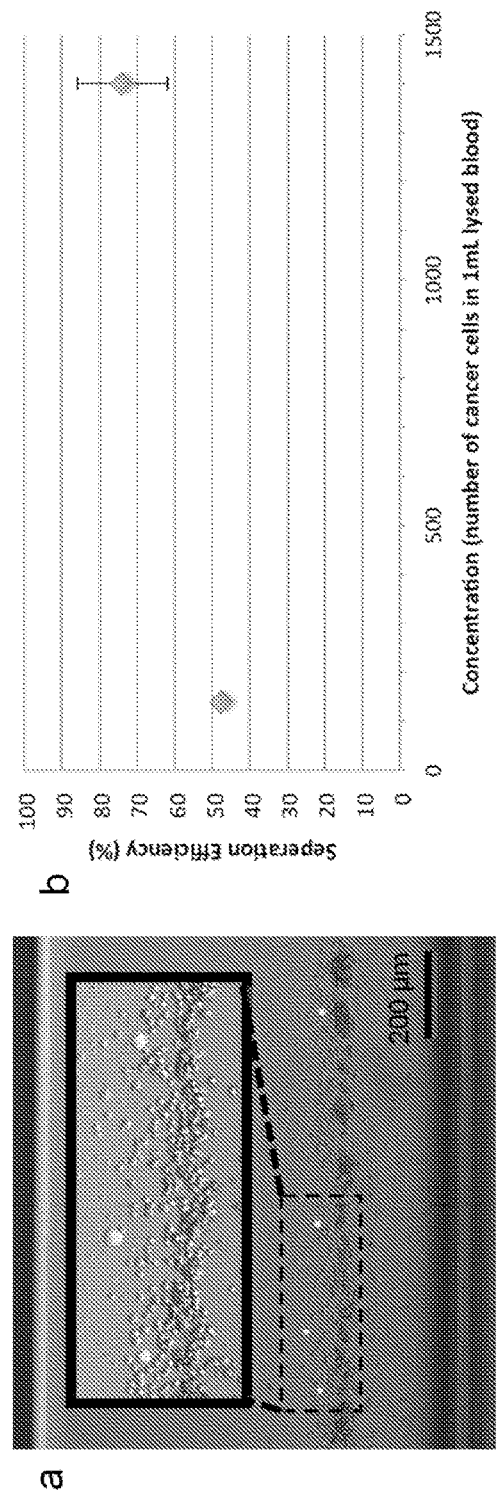
FIG. 10 illustrates the separation efficiency of breast cancer cells.

Looking at FIG. 10, the separation efficiency of breast cancer cells is illustrated. It is demonstrated that the cancer cells spiked in blood samples can be separated in high efficiency from blood cells. In FIG. 10*a*, a micrograph is provided in which fluorescently-labeled breast cancer cells (MDA) are spiked in blood and separated using the levitation system. The inset panel of FIG. 10*a* shows three large dots which are the labeled MDAs. FIG. 10*b* illustrates the separation efficiency of breast cancer cells spiked in blood cells at different concentrations. This data establishes that the levitation system can be easily applied for CTC and CTM quantification for cancer diagnostic and prognostic applications.

Figure 11:
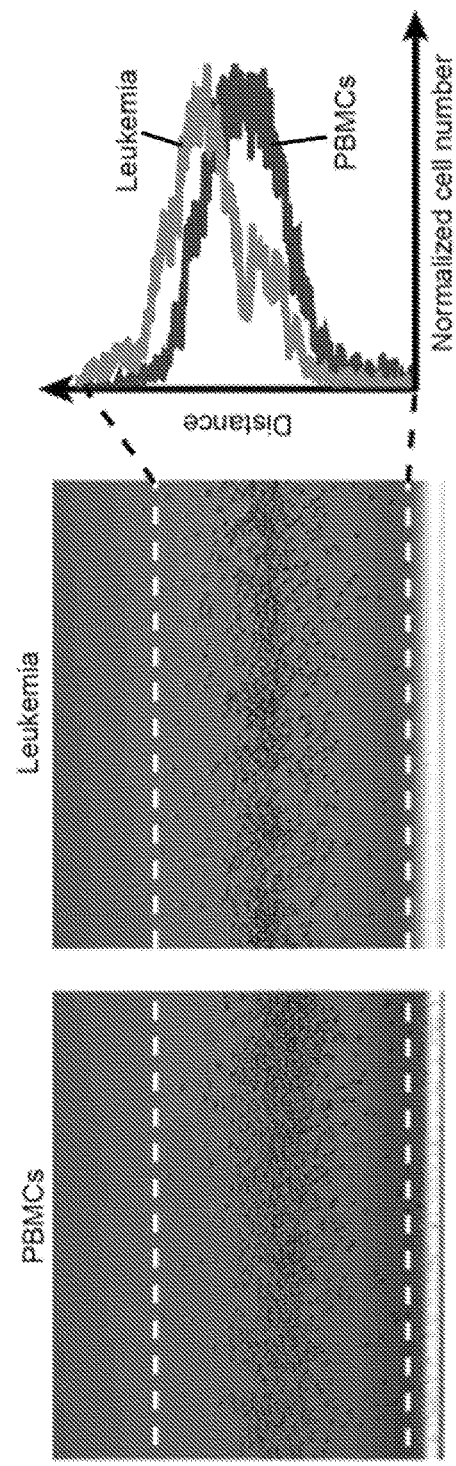
FIG. 11 illustrates the observed profile of peripheral blood mononuclear cells (PBMCs) of healthy and leukemia patients.

The device is also capable of identification of other cancer cells from blood cells. For instance, as illustrated in FIG. 11, peripheral blood mononuclear cells (PBMCs) of healthy and leukemia patients exhibit different cellular profiles upon separation (i.e., the height of the leukemia cells is higher than that height of the PBMCs).

Figure 12:
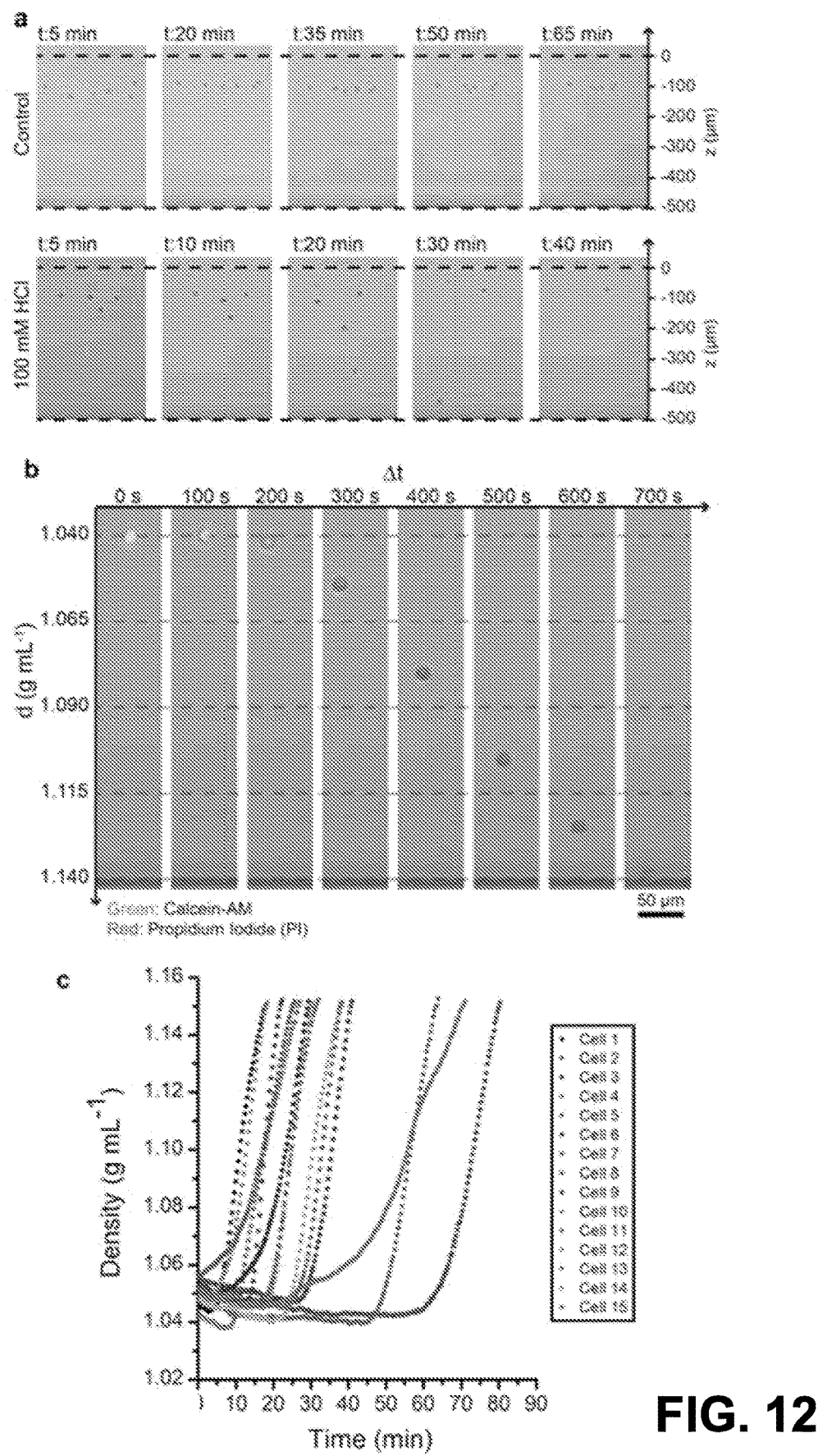
FIG. 12 illustrates the real-time density changes of single cells after application to hydrochloric acid (HCl).

Example 7: Real-Time Monitoring of Response of Cells to the Environmental Factors in a Single Cell Level As illustrated in FIG. 12, real-time monitoring of the response of cells to the environmental factors can be performed at a single cell level. In particular, FIG. 12 illustrates the real-time density changes of single cells after application to hydrochloric acid (HCl).

FIG. 12*a* shows micrographs of control (untreated) and HCl-treated MDA breast cancer cells in which the control cells maintain their levitation height (i.e., density), but in which the HCl-applied cells sink to the bottom of the channel (i.e., z=−500 μm) over 40 minutes of exposure to 100 mM HCl.

FIG. 12*b* details the real-time observation of a HCl-applied single cell in which a viability assay was also conducted using Calcein (green fluorescent) for live cell and Propidium Iodine (red fluorescent) for dead cell. Fluorescent images and bright field images were overlapped each other to compose the micrographs at different time point. While the cell is sinking through the channel bottom and it is gaining density, the fluorescent profile on the cell is changing from green to red indicating a dying cell. This shows in real-time, over the span of 700 seconds, the death of the cell and the correlation of this cell death to a density change and levitational height change.

FIG. 12c shows real-time density measurement of acid-treated single cells in which it is illustrated that, even if the acid is applied to the cells at the same time, each of the cells behave differently due to cellular heterogeneity.

By way of this example, it is illustrated how the effect of environmental factors (e.g., pH, temperature, chemicals, and so forth) on cells can be monitored as cellular density changes. This can be used to analyze cellular heterogeneity, which is helpful for understanding cancer, immune response, infectious diseases, drug resistance and evolution.

Example 8: Real Time Monitoring for Drug-Screening Applications

Figure 13:
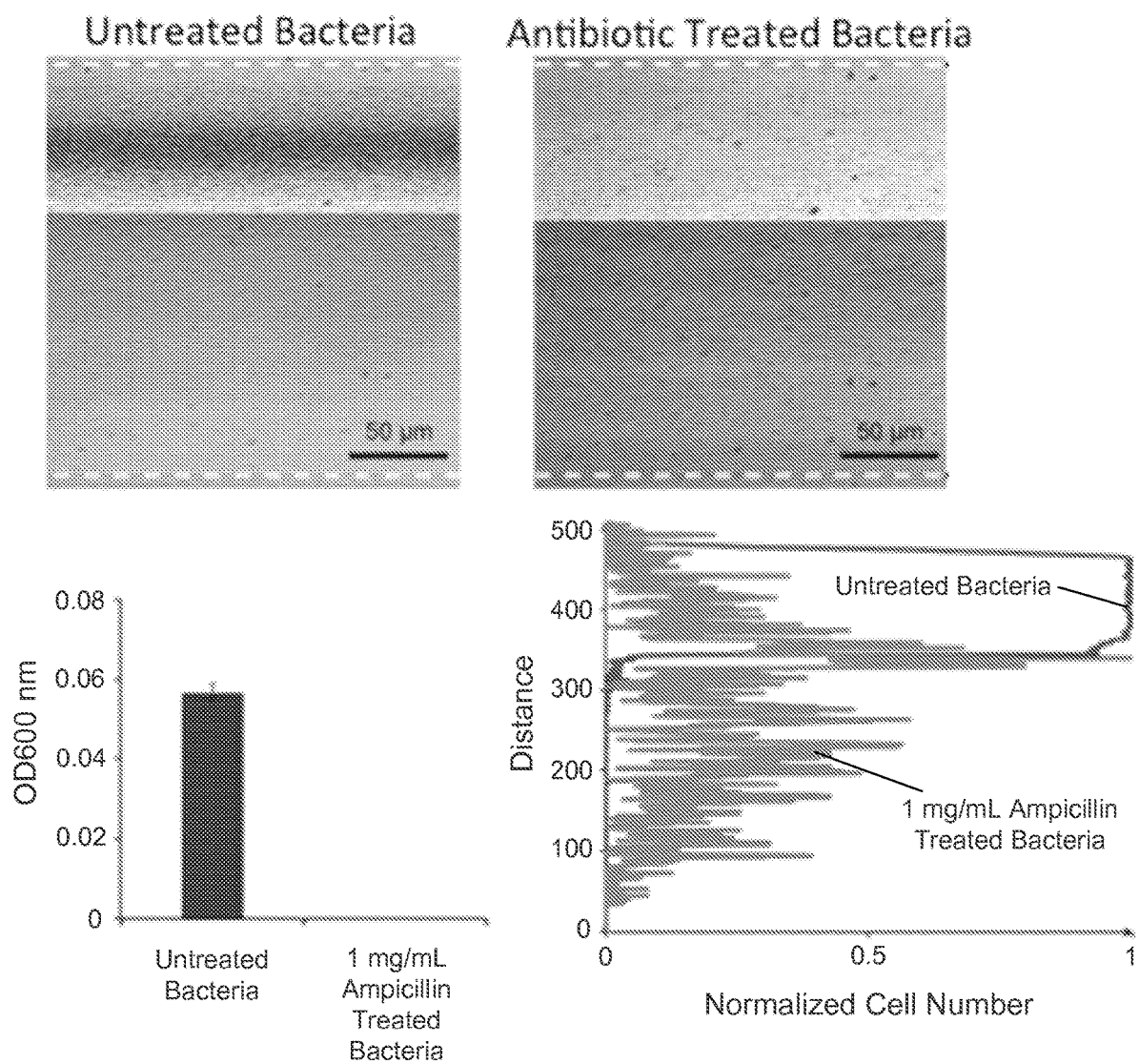
FIG. 13 illustrates comparative height distribution profiles obtained using the magnetic levitation-mediated platform of untreated and ampicillin-treated bacteria (i.e., *E. coli*) cells, in terms of magnetic levitation heights. Live and dead bacterial cells have distinct magnetic profiles that can be detected rapidly in real-time.
Figure 14:
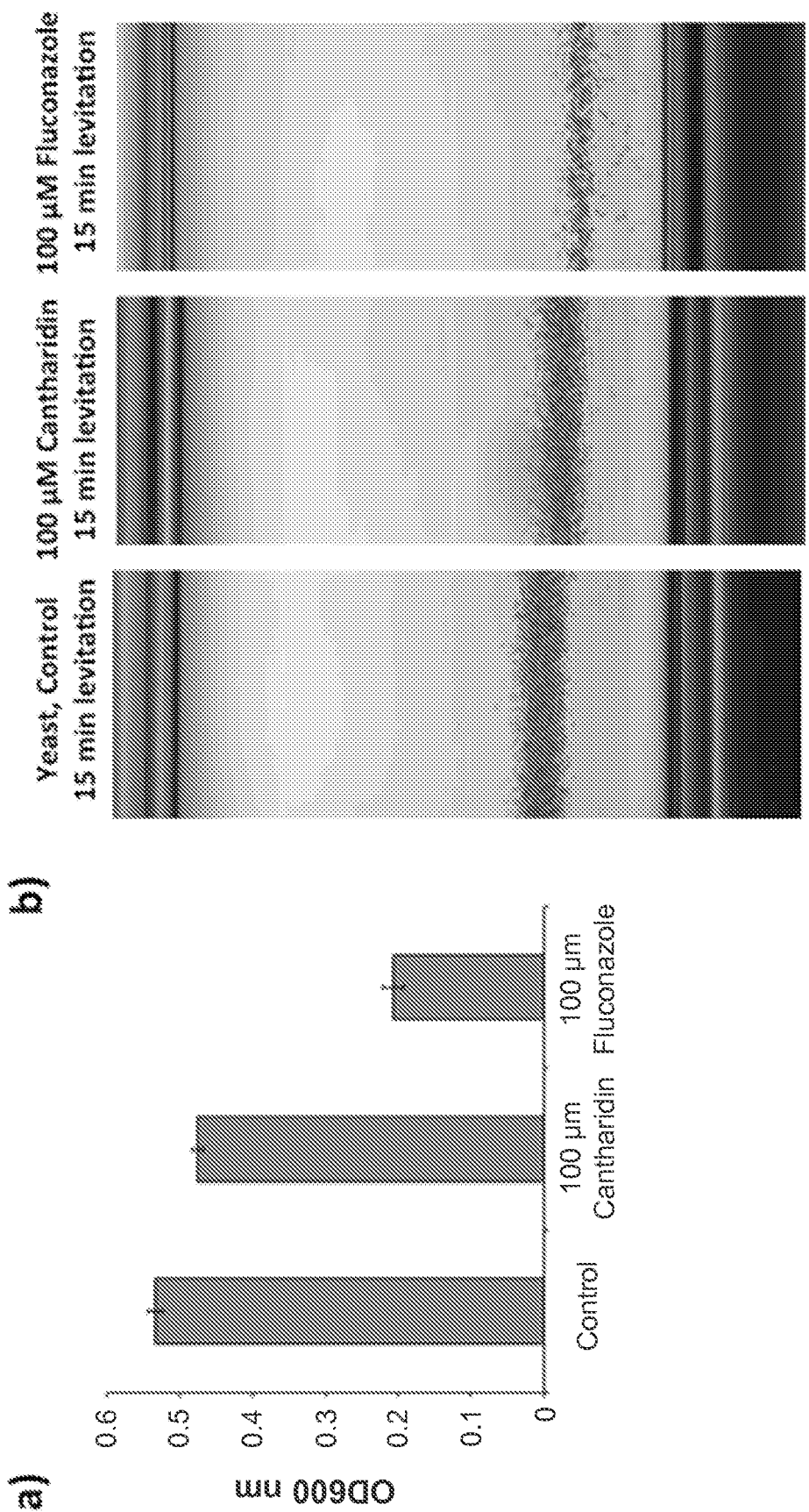
FIG. 14 illustrates magnetic levitation and characteristics of yeast cells.
Figure 15:
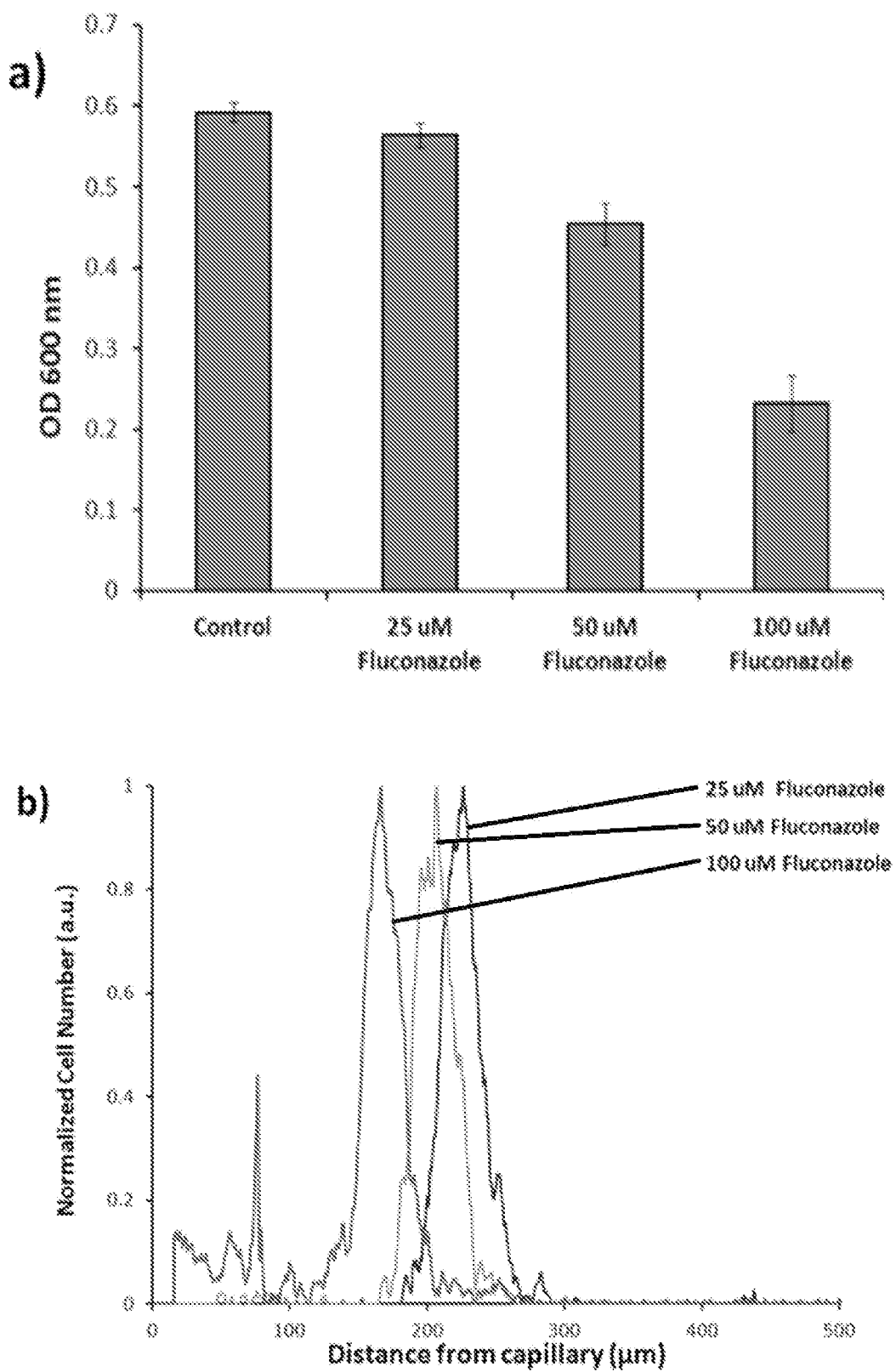
FIG. 15 provides data relating to the observed drug responses and observed changes in magnetic profile of cells.
Figure 15:
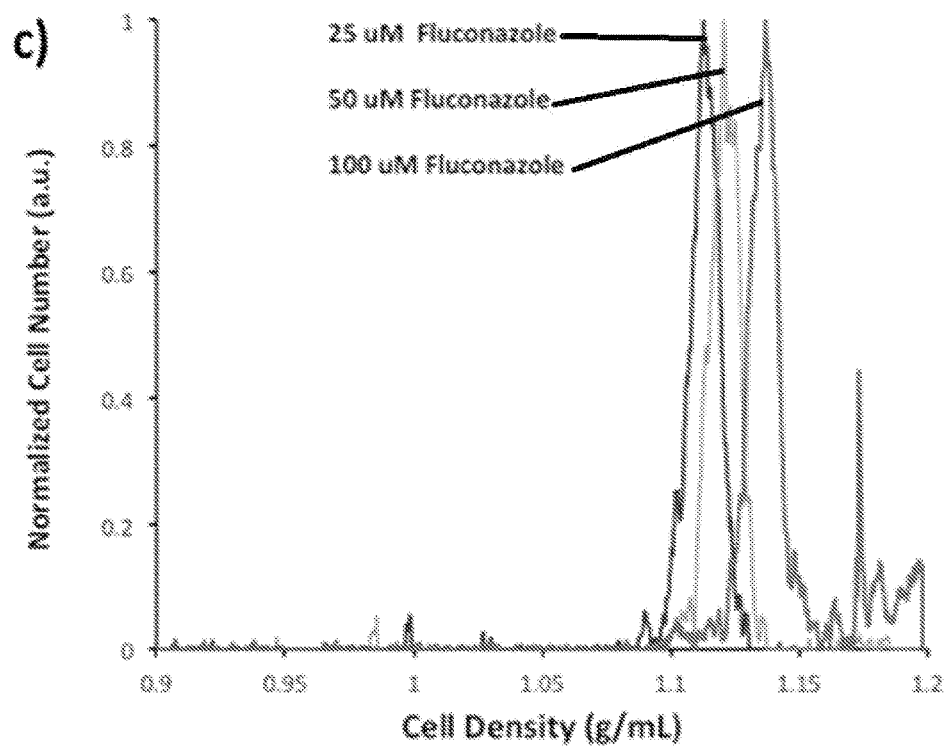
Figure 15:
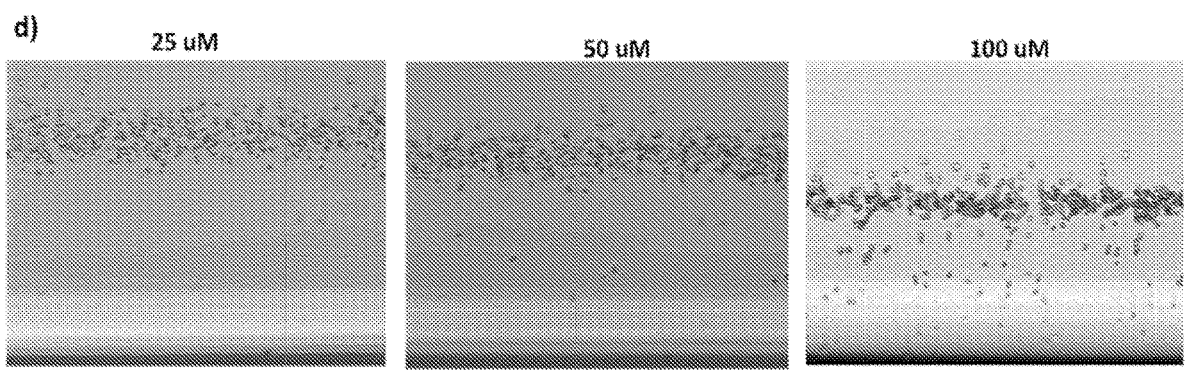

The levitation system also permits real-time assessment of cellular profiles after drug treatment for drug-screening applications (i.e., antibiotics, chemotherapy) as illustrated generally in FIGS. 13-15. Changes in the cellular profile during infections as well as during drug treatment (i.e., antibiotics, anti-fungal drugs, anti-cancer agents) can be observed rapidly using the magnetic levitation system.

As illustrated in FIG. 13 (and, in particular, the lower right panel of FIG. 13), the magnetic levitation-mediated platform was used to detect significant differences between untreated and ampicillin-treated bacteria (i.e., E. coli) cells, in terms of magnetic levitation heights. As the bacteria respond to the stimuli and antibiotics, their density are altered. This directly reflects on their levitation heights.

Similar techniques can be used in real-time to monitor the emergence of antibiotic-resistance in bacteria. Antibiotic resistance can be assessed by monitoring the live/dead bacteria as a function of their levitation heights that change in observed cellular density which are dynamically altered post-exposure to antibiotics.

Looking at FIG. 14, the magnetic levitation and characteristics of yeast cells are illustrated that have either not been exposed or have been exposed to various drug treatments for some duration of time. FIG. 14a graphs the viability of yeast cells after different drug treatments (i.e., no drug treatment/control, 100 µM cantharidin, or 100 µM fluconazole) for 24 hours. Different viabilities are observed and optical densities are indicated for the various drug treatments. FIG. 14b provides micrographs illustrating how, after 15 minutes of magnetic levitation, the levitation heights, magnetic properties and intrinsic magnetic signatures of yeast cells are altered after drug treatment with 100 µM cantharidin and 100 µM fluconazole for 24 hours.

Turning now to FIG. 15, this figure provides data relating to the observed drug responses and observed changes in magnetic profile of cells. FIG. 15a shows optical density (OD) profiles after various types of drug exposure (i.e., control, 25 µM fluconazole, 50 µM fluconazole or 100 µM fluconazole). FIG. 15b shows cellular distribution inside the channel and FIG. 15c shows calculated single-cell densities. FIG. 15d provides various micrographs of cells treated with different concentration of drug (fluconazole), the treatment concentration being listed above each micrograph. It is observed that cellular magnetic profiles and densities change after treatment with different drug concentrations (both in height and spread, which are indicative of health and variance in heath of cells, respectively). It is further noted that these changes can be monitored with the magnetic levitation system at the single-cell level.

Figure 21:
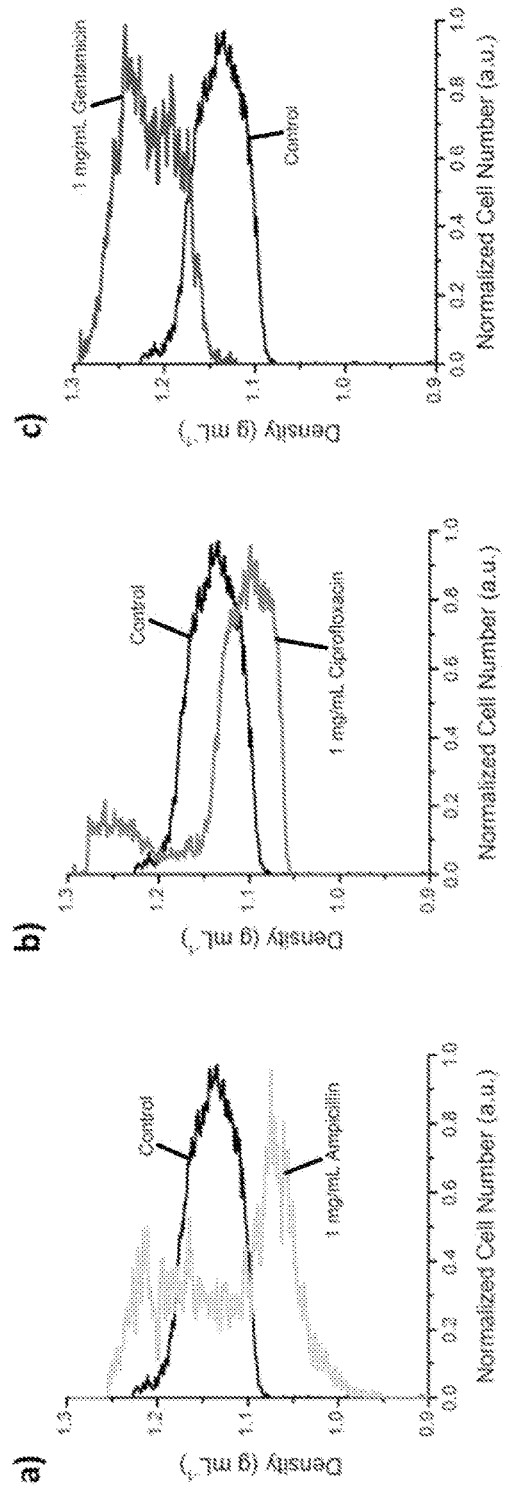
FIG. 21 illustrates changes in magnetic levitation profiles during antibiotic treatment. *E. coli* cells were treated two hours with different classes of antibiotics; 1 mg/mL of ampicillin (beta-lactam antibiotic) as in FIG. 21a, ciprofloxacin (fluoroquinolone antibiotic) as in FIG. 21b, and gentamicin (aminoglycoside antibiotic) as in FIG. 21c.

With forward reference to FIG. 21, differences are illustrated in the observed magnetic levitation profiles of E. coli cells after different types of antibiotic treatment. The E. coli cells were treated for two hours with different classes of antibiotics including 1 mg/mL of ampicillin (beta-lactam antibiotic), ciprofloxacin (fluoroquinolone antibiotic), and gentamicin (aminoglycoside antibiotic). The magnetic levitation profile of each of these antibiotics are compared to a control (i.e., untreated E. coli cells) in FIGS. 21a, 21b, and 21c, respectively. This data illustrates that different antibiotic treatments change the levitation heights and cellular magnetic profiles in a different manner.

Figure 22:
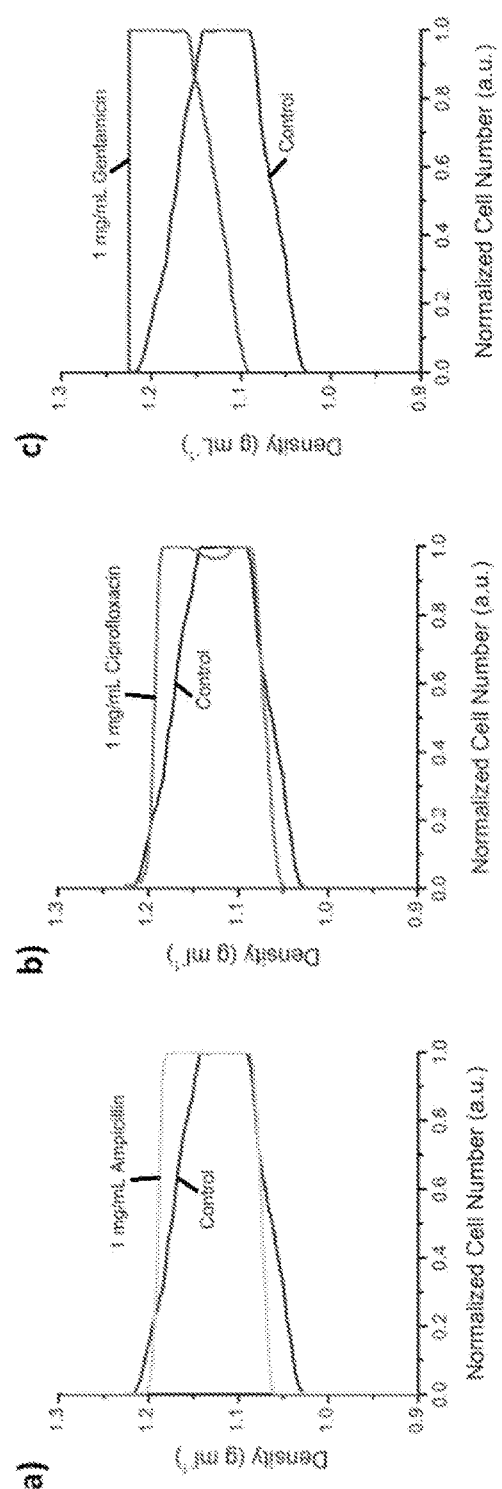
FIG. 22 illustrates changes in magnetic levitation profiles of multi-drug resistant bacteria during antibiotic treatment. The effects of different antibiotics including ampicillin, ciprofloxacin, and gentamicin, as in FIGS. 22a, 22b, and 22c, respectively, on multi-drug resistant *E. coli* was investigated using the magnetic levitation system.

With additional forward reference to FIG. 22, differences are illustrated in the observed magnetic levitation profiles of multi-drug resistant E. coli cells after different types of antibiotic treatment. In these experiments, the effects of different antibiotics (ampicillin, ciprofloxacin, and gentamicin, respectively) on multi-drug resistant E. coli were investigated using the magnetic levitation system. This clinical isolate is resistant to ampicillin and ciprofloxacin, but is susceptible to gentamicin. Accordingly, there was no significant change in levitation heights and magnetic levitation profiles after two hours treatment with 1 mg/mL ampicillin and ciprofloxacin as illustrated in FIGS. 22a and 22b, respectively. On the other hand, there was a noticeable change in the levitation heights and magnetic levitation profiles after treatment with 1 mg/mL gentamicin for two hours as is illustrated in FIG. 22c.

Thus, the magnetic levitation system has the potential to test the efficacy of antibacterial treatments and the magnetic levitation system can be used for antibacterial susceptibility testing applications.

Example 9: Real-Time Monitoring of Emergence of Drug-Resistance in Cancer Cells

These same type of techniques can be used to, in real-time, monitor the emergence of drug-resistance in cancer cells: Drug resistance in cancer cells can be assessed by monitoring the levitation heights that change in their cellular profiles observed during magnetic levitation that are dynamically altered post-exposure to anti-cancer agents. It is contemplated that the efficacy of drug treatment can be also investigated using these real time methods.

Example 10: Real-Time Detection of Cellular Heterogeneity at the Single-Cell Level Notably, this technology enables the real-time detection of cellular heterogeneity at the single-cell level as illustrated in FIG. 12 and establishes that different cells may respond differently as the result of many cellular factors.

Likewise, this means that the heterogeneity of drug responses of different cells can be monitored in real-time at single-cell resolution. For example, real-time density measurement of acid-treated single cells were conducted and variance in the response of the cells was observed given the single cell resolution. Even though the acid was applied to the cells at the same time, each cells behaved differently due to the cellular heterogeneity as is acutely illustrated in FIG. 12c.

Accordingly, using this real-time levitation system, it is contemplated that certain groups of cells may be first characterized and then treated. This variance in cell behavior across a population of cells may be intrinsic, but the ability to monitor the cells at a single cell resolution, in response to the variance of environmental factors or in response to variable treatment conditions, provides a complex and sophisticated way to study the way that a population cells respond which could be invaluable to a better understanding the underlying mechanisms, behaviors, and responses in these systems and provides a powerful assaying tool.

Example 11: Detection and Separation of Live and Dead Cells

Further to the experimental results observed in FIGS. 12 and 13, live and dead cells can be separated using this platform. This potentially permits for both detection and characterization of cell populations or potentially the separation of the live and dead cell populations from one another. Such detection and sorting might be incorporated into testing protocols or to selectively obtain certain varieties of cell samples.

Example 12: Profile of Cell Cycle and of Cellular Senescence and Aging

The system or platform also can be used as a tool to observe cell cycles and may be used to characterize certain types of cells based on their observed behavior.

Figure 16:
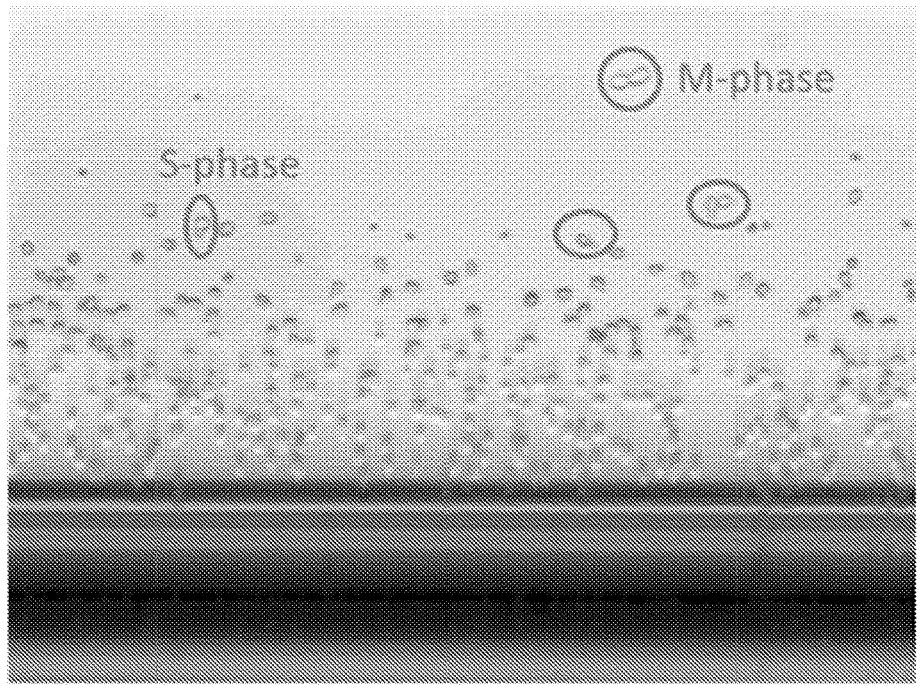
FIG. 16 illustrates that budding yeast cells have different densities during different phases of cell cycle and have distinct magnetic profiles. Mass, density, and volume of cells (i.e., *Saccharomyces cerevisiae*) through the cell cycle can be measured by monitoring their levitation heights.

As illustrated in FIG. 16, budding yeast cells have different densities during different phases of cell cycle. In addition, this platform has demonstrated that observed profiles of the cells (i.e., yeast cells) change during the cell cycle. For example, as illustrated in FIG. 16, yeast cells at M-phase had a greater levitation height than the cells at S-phase.

Figure 17:
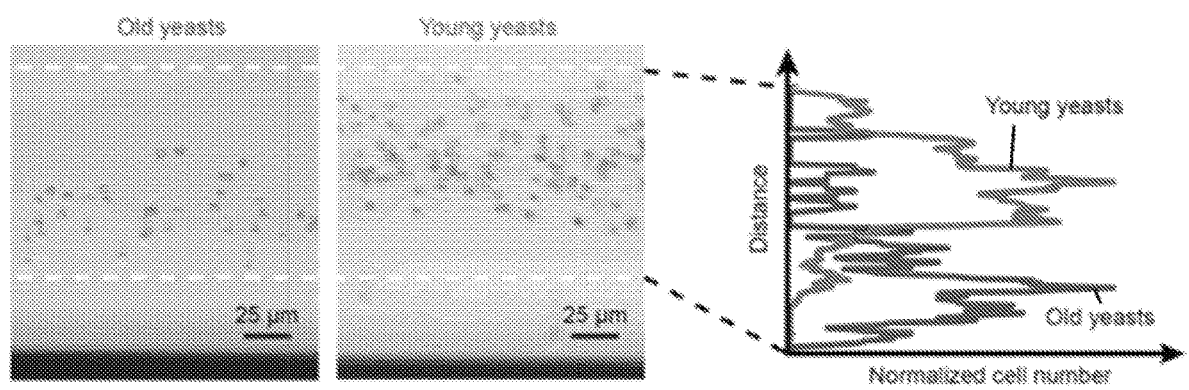
FIG. 17 provides magnetic profiles collected illustrating cellular senescence and aging. The younger yeast cells are isolated by centrifuging at 1400 rpm, while the older cells are isolated by centrifuging at 900 rpm and 1400 rpm, respectively. Once they are isolated at the respected centrifugation speeds, the disclosed cellular levitation device has shown that young and old cell populations have different cellular magnetic profiles and levitate at different heights.

Further observed profiles are provided in FIG. 17 illustrating cellular senescence and aging in yeast. As yeast cells age, many physical and biological changes occur. For example, cell size increases, cell cycle slows down, cell shape is altered, cell nucleolus tends to be larger and/or more fragmented, and cells become sterile. The provided micrographs of old yeasts and young yeasts (left and center panels, respectively) illustrate that younger and older yeast populations are different profiles. These profiles can be further characterized as in the rightmost panel in which the normalized cell number is provided at various the levitation heights (i.e., distances). Thus, two very different profiles can be generated and compared as in the rightmost panel to illustrate the health of a particular cell group and, furthermore, due to the real-time nature of the data collection, can be used to create sequenced profiles characterizing the aging of the observed cell population.

Example 13: Microorganism and Pathogen Identification

Figure 18:
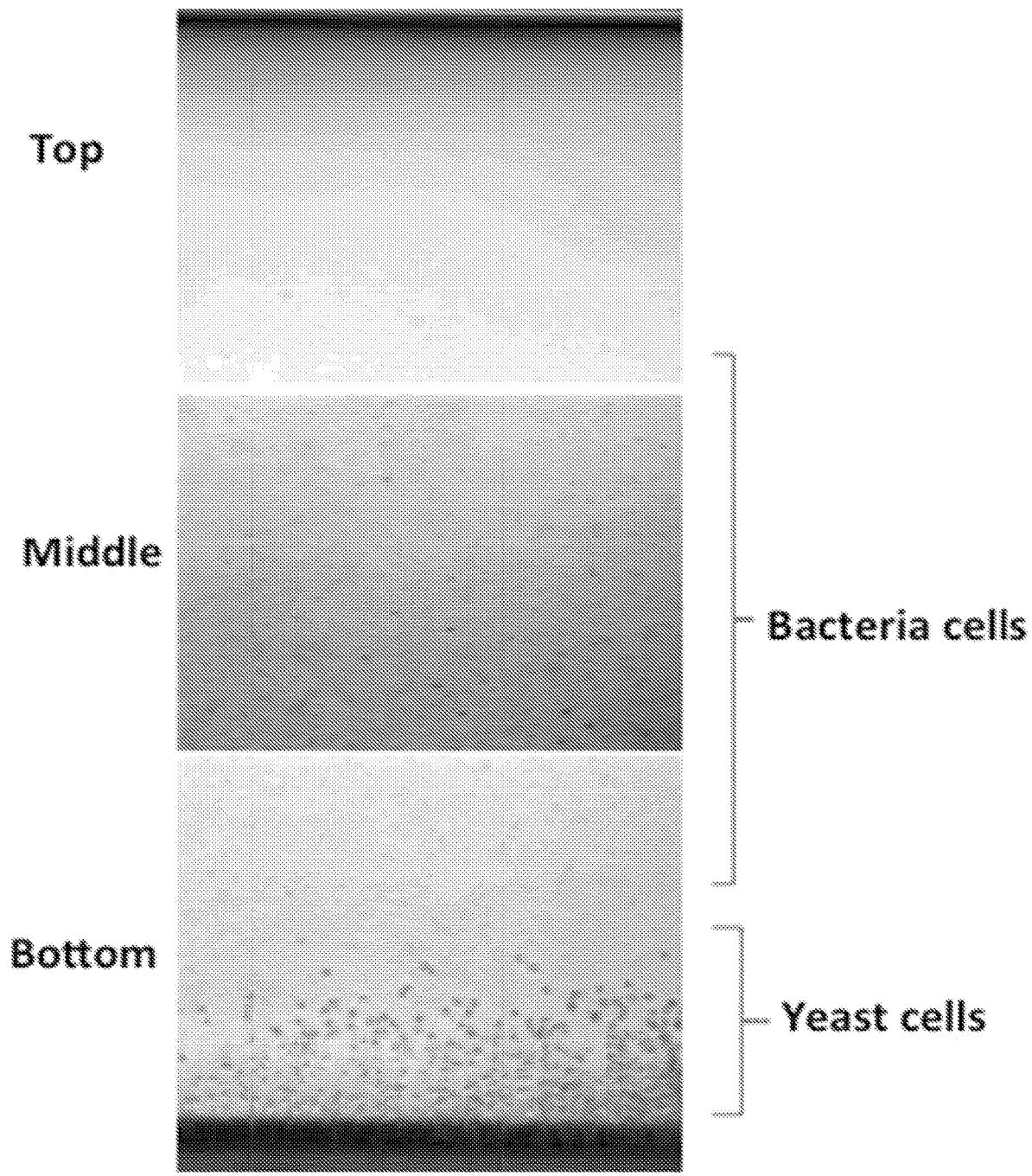
FIG. 18 details how the cellular levitation device can be used to identify microorganisms. Yeast and bacteria cells are shown in FIG. 18 to have different characteristic magnetic profiles; accordingly, individual microorganisms can be identified and separated from a mixed culture at low concentrations according to their densities using the magnetic levitation-based platform.

As illustrated in FIG. 18, this platform and system can also be used to identify microorganisms and pathogens. Individual microorganisms (i.e., bacterial yeast, fungi, virus) can be identified and separated from a mixed culture at low concentrations according to their magnetic signatures using the magnetic levitation-based platform. For example, yeast and bacteria cells have different characteristic magnetic distributions or profiles. As illustrated in FIG. 18, with the system in used, the middle of the channel includes primarily bacteria cells, while the bottom of the channel includes primarily yeast cells.

Example 14: Distinguishing Gram-Positive and Gram-Negative Bacterial Species Using Magnetic Profiles It is further contemplated that gram-positive and gram-negative bacterial species can be distinguished using magnetic profiles and cellular distributions. Gram-positive and gram-negative bacteria have different surface properties. For example, gram-positive bacteria cell wall consists of a thick layer of peptidoglycan (20-80 nm) and teichoic acids. Gram-negative bacteria cell wall is much more complicated, composed of an outer membrane (7-8 nm) and a thin layer of peptidoglycan (1-3 nm). In addition, gram-negative bacteria have a higher lipid and lipoprotein content due to the presence of an outer membrane as well as the lipopolysaccharides (LPS). Thus, gram-negative and gram-positive bacteria have different densities due to the different compositions of cell walls and these differences can be detected and monitored in real-time using magnetic levitation principles.

Example 15: Viral Infection Detection on Cells

Figure 19:
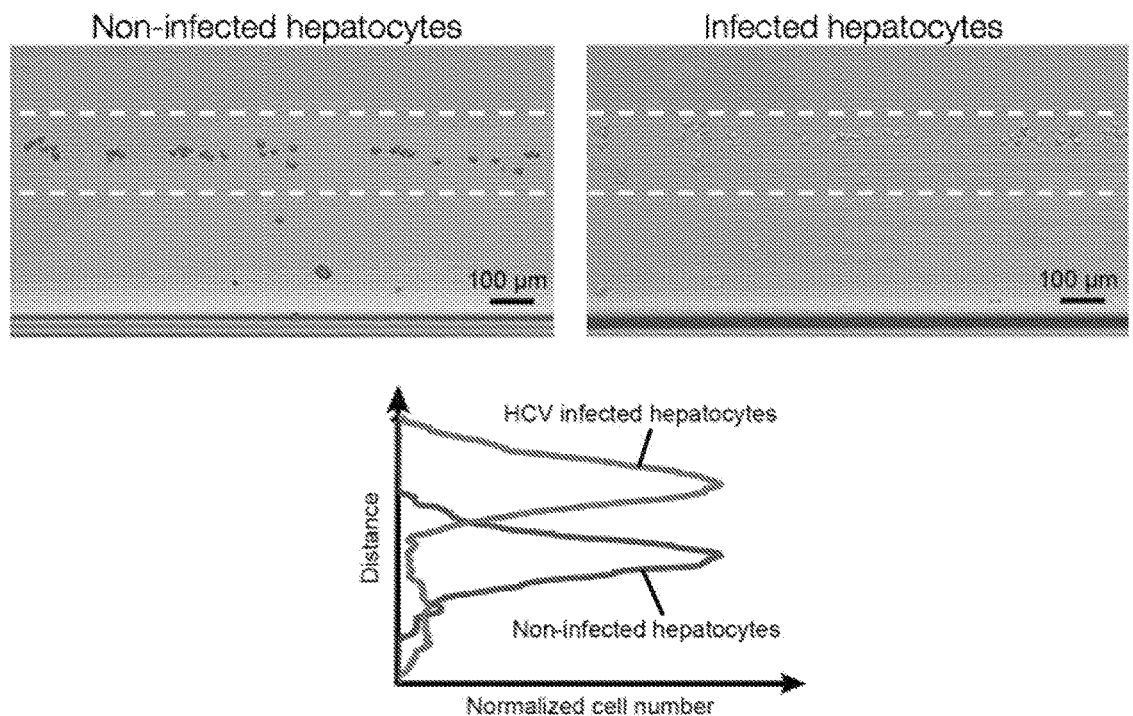
FIG. 19 provides micrographs and corresponding magnetic profiles of healthy and hepatitis C virus (HCV) infected hepatocytes. Infected cells are clearly distinguished from healthy cells by density and magnetic profiles.

With reference to FIG. 19, micrographs and corresponding magnetic profiles are provided of healthy and hepatitis C virus (HCV) infected hepatocytes. Infected cells are clearly distinguished from healthy cells by density and magnetic profiles. This data clearly shows that the magnetic separation profile of hepatocytes cells change significantly when they are infected with hepatitis C virus (HCV) as illustrated in the lowermost panel.

Example 16: Early Diabetes Detection

Figure 20:
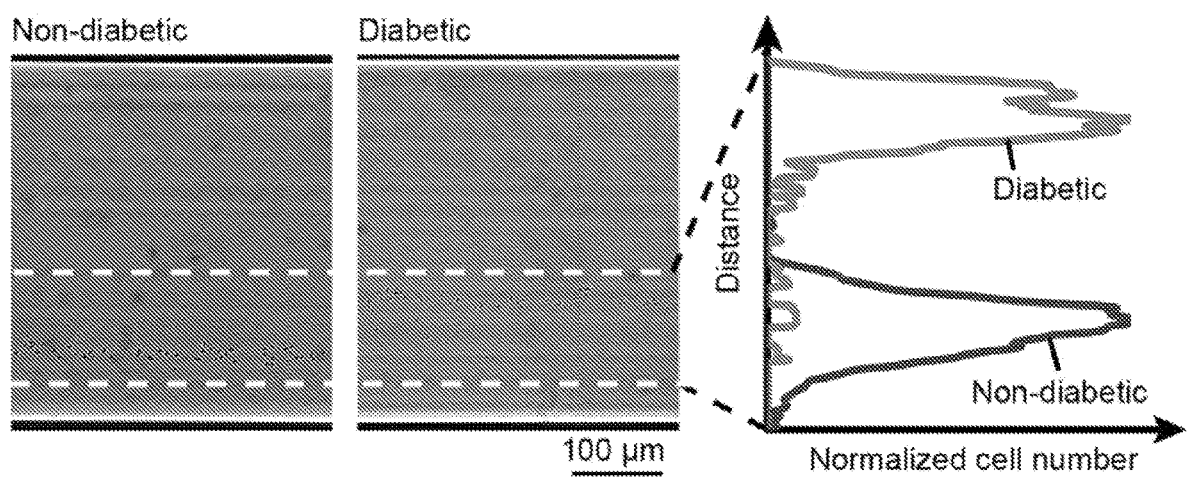
FIG. 20 provides magnetic profiles of RBCs of non-diabetic and diabetic mice (type I diabetes).

Finally, other types of cellular changes can also be observed using the platform. In FIG. 20, magnetic profiles of red blood cells of non-diabetic and diabetic mice (type I diabetes). Blood cells type I diabetes mice show different cellular density profiles than the blood cells from the healthy cells. Accordingly, this device offers a new way for early diagnosis of diabetes by monitoring changes in levitation heights.

In the examples above, the following antibodies and reagents were utilized: Hoecsht 33342 (H1399, Molecular Probes, Eugene, Oreg.); Hank's Balanced Salt Solution (14025-092), Cell Mask Deep Red plasma membrane stain (C10046), Cell Tracker Green, CMFDA (C-7025), NPE-caged ATP (A-1048, Life Technologies, Grand Island, N.Y.); FICOLL® (17-5442-03), PERCOLL® (17-0891-01, GE Healthcare, Pittsburgh, Pa.); citrate 4% w/v (S5770), Dextran T500 (31392), Glutathione reduced ethyl ester (GSH-ME, G1404), Sodium metabisulfite (S9000), Sodium Chloride (S5886, Sigma, St. Louis, Mich.); Phorbol 12-myristate 13-acetate (PMA, 1201, Tocris, Bristol, United Kingdom); VITROTUBES™ Square Capillary Microcells, Borosilicate Glass (8100, Vitrocom, Mountain Glass, N.J.); Gadolinium-based (Gd+) paramagnetic medium PROHANCE® (Gadoteridol from Bracco Diagnostics, Princeton, N.J.); CRITO-SEAL™ (a capillary tube sealant including vinyl plastic from Fisher Scientific, Pittsburgh, Pa.).

In the examples above, to load samples into a microcapillary tube, microcapillaries were simply dipped into the sample vials, and sample filled into the capillary due to capillary forces. For each experiment, new microcapillary was used. Further, unless otherwise stated, cells were resuspended in 200 µL of 40 mM Gadolinium solution and loaded in 1.0×1.0 mm square microcapillary tubes (wall thickness 0.2 mm) by superficial tension action. Critoseal™ was inserted into either end of the microcapillary to prevent cells from drifting during analysis. The capillary was then loaded into a slot between the magnets and cells were imaged using either QImaging Emc$^2$ EMCCD camera on an Olympus BX62 microscope or a Qimaging EXi CCD camera on a Zeiss Axioscope microscope. For high-resolution images, a fluorescence microscope leveled on its side was perfectly horizontally placed, and used a mirror-free magnetic levitation setup. The images were analyzed with Slidebook 5.5. (3i, Denver, Colo.), ImageProPlus 7 (Media Cybernetics, Rockville, Md.), and iVison 4.7 (Biovision, Exton Pa.).

By virtue of these examples, the versatility of the microfluidic, magnetic levitation platform that allows separation and activation of cells, as well as monitoring and quantifying of various morphological attributes, specific cellular activities and agonist responses in real-time has been demonstrated. The strategy presented here allows examination of temporal responses of cells to bioactive mediators introduced by caged compounds (such as, for example, ATP). The advantages of the system include, but are not limited to (i) simple workflow, (ii) lack of sophisticated micro/nano-fabrication components, (iii) disposable designs with the possibility for autoclaveable reusable modules, and (iv) multi-dimensional, real-time quasi-physiological investigation of dynamic cell:cell communications such as antigen-presenting cell:T cell and platelet:monocyte interactions.

The magnetic levitation device offers numerous biotechnology applications as well as a platform to study and monitor several fundamental cellular behavior. It provides unique capabilities for cell biology research where cell densities matter, and can reflect various processes such as cell-cycle, phagocytosis, apoptosis, and differentiation. This system is also sensitive to magnetic susceptibilities of cells, and can thus be used for analysis of hemoglobin degradation within the RBCs (for example, stored blood and sickle cells). The capability of monitoring several cellular activities can be also significant for drug discovery, toxicity testing, and single cell testing. Real-time monitoring of levitating cells, followed by protein and nucleic acid analyses, will potentially open avenues for research in unique signaling mechanisms present only during low gravity conditions.

This platform allows for measurements of cell densities (for example, RBCs, white cells) and separation of cells based on the balance between corrected gravitational force and counter-acting magnetic force. Simplicity, small size-scale and flexibility of the design make the system also compatible with mobile devices for telemedicine and use in resource poor settings for screening and diagnostics of malaria-infected red blood cells and sickle cells. This strategy does not require antibodies, advanced microscopy instrumentations or techniques for reliable diagnosis, nor the presence of microscopy specialists. This strategy holds great promise for identification, isolation and in-depth omics data analyses of subpopulation of cells in a variety of normal and pathological conditions.

The present invention has been described in terms of one or more preferred embodiments, and it should be appreciated that many equivalents, alternatives, variations, and modifications, aside from those expressly stated, are possible and within the scope of the invention.

What is claimed is:

1. A method for separating a heterogeneous population of cells, the method comprising the steps of:
    placing a microcapillary channel containing a sample of the heterogeneous population of cells in a magnetically-responsive medium into a levitation system, wherein the system comprises
        a set of two magnets producing a magnetic field, wherein a space between the two magnets is sized to receive the microcapillary channel in a horizontal orientation relative to the direction of gravity, wherein the magnetic field is spatially constant over a distance of the microcapillary channel between the two magnets; and
        a microscopy device having a stage between the set of two magnets on which the microcapillary channel is placed; and
    levitating the heterogeneous population of cells in the magnetically-responsive medium by balancing a magnetic force applied to each of the cells by the magnetic field of the magnets with a corrected gravitational force of the cells in the magnetically-responsive medium, thereby separating the heterogeneous population of cells.

2. The method of claim 1, wherein the heterogeneous population of cells are differentiated from others in at least one of their magnetic susceptibility and cell density, and a cell variant creates this difference, wherein
    the cell variant is selected from the group consisting of cell type, cell-cycle stage, malignancy, disease state, activation state, cellular age, infection state, cellular differentiation, apoptosis of the cell, and phagocytosis of the cell.

3. The method of claim 1, further comprising the step of separating the individual cells to an equilibrium exhibiting a balance between gravitational forces and magnetic forces on the individual cell.

4. The method of claim 1, wherein the heterogeneous population of cells is selected from a group consisting of red blood cells, leukocytes, lymphocytes, phagocytes, platelets, and cancer cells.

5. The method of claim 1, wherein the levitation system comprises a first mirror on a first open side of the microcapillary channel and a second mirror on a second open side of the microcapillary channel in which the mirrors are oriented at oblique angles relative to the path between the mirrors, and wherein
    the method further comprises the step of reflecting light from a light source within the microscope with the first mirror through the sample of cells and towards the second mirror.

6. The method of claim 1, wherein the microscopy device is an upright fluorescence microscope leveled horizontally on its side, a side-viewing microscope, a cell phone camera, a lensless charged-coupled device (CCD) or complementary metal-oxide semiconductor (CMOS) system, or an inverted microscope.

7. The method of claim 1, wherein the magnetically-responsive medium is a paramagnetic medium and comprises gadolinium.

8. The method of claim 7, wherein the magnetically-responsive medium comprises a gadolinium-based medium wherein gadolinium is present at a concentration of 20 to 100 mM.

9. The method of claim 1, wherein the method is performed at the point of care, and wherein the magnetic field does not interfere with mobile devices.

10. The method of claim 1, wherein the magnetic field includes a magnetic field gradient created by electrical magnets using alternating currents.

11. The method of claim 1, wherein the set of two magnets are permanent magnets in an anti-Helmholtz configuration.

12. The method of claim 1, further comprising the step of observing the heterogeneous population of cells are in real time by the microscopy device, the microscopy device providing various images of the heterogeneous population of cells over a duration of time.

13. The method of claim 12, further comprising the steps of altering a physical environment of the heterogeneous population of cells and of observing a response of the heterogeneous population of cells as a result of the physical environment.

14. The method of claim 12, further comprising the steps of introducing a treatment agent into the heterogeneous population of cells and of observing a response of the heterogeneous population of cells as a result of the treatment agent.

15. The method of claim 12, wherein individual cells in the heterogeneous population of cells are individually monitored and tracked during the step of observation.

16. The method of claim 12, wherein the step of observation includes monitoring the heterogeneous population of cells during different phases of the cell life cycle.

17. The method of claim 14, wherein observing a response of the heterogeneous population of cells as a result of the treatment agent includes monitoring a continued response of the heterogeneous population of cells to establish the emergence of resistance of the heterogeneous population of cells to the treatment agent.

18. The method of claim 14, wherein the treatment agent is a drug.

19. The method of claim 14, wherein the treatment agent is an antibiotic.

20. The method of claim 1, wherein the heterogeneous population of cells includes some cells that are infected with a virus.

21. The method of claim 1, wherein the heterogeneous population of cells are levitated in a patient sample.

22. The method of claim 21, wherein the patient sample is blood.

23. The method of claim 21, wherein the cancer cells are separated from healthy cells.

24. The method of claim 21, wherein red blood cells are levitated to detect the presence of type I diabetes.

25. The method of claim 1, wherein, during the levitation step, live cells in the heterogeneous population of cells are separated from dead cells.

26. The method of claim 25, wherein, the separation of live cells from dead cells in the heterogeneous population of cells are used to determine the efficacy of a treatment agent.

27. The method of claim 25, wherein, the separation of live cells from dead cells in the heterogeneous population of cells are used to determine the effect of a change in the physical environment on the cells.

28. The method of claim 1, wherein, during the step of separation, different microorganisms are separated from one another.

29. The method of claim 1, where a characteristic of at least some of the heterogeneous population of cells is determined by a measured height of the cells in the microcapillary channel.

30. The method of claim 1, wherein the cell reaches its equilibrium levitation height within the microcapillary within 10 minutes.

31. The method of claim 1, wherein the cell reaches its equilibrium levitation height within the microcapillary within 15 minutes.

32. The method of claim 1, wherein a direction of separation of the heterogeneous population of cells during the step of levitation is perpendicular to a direction of flow of the sample of the heterogeneous population of cells in a magnetically-responsive medium through the microcapillary channel.

33. The method of claim 1, wherein the two magnets are vertically positioned with respect to one another with the microcapillary channel placed therebetween relative to the direction of gravity.

34. A method for real-time interrogation of cells, the method comprising the steps of:
placing a microcapillary channel containing a sample of the heterogeneous population of cells in a magnetically-responsive medium into a levitation system, wherein the system comprises
a set of two magnets producing a magnetic field, wherein a space between the two magnets is sized to receive the microcapillary channel in a horizontal orientation relative to the direction of gravity, wherein the magnetic field is spatially constant over a distance of the microcapillary channel between the two magnets; and
a microscopy device having a stage between the set of two magnets on which the microcapillary channel is placed; and
levitating the heterogeneous population of cells in the magnetically-responsive medium by balancing a magnetic force applied to each of the cells by the magnetic field of the magnets with a corrected gravitational force of the cells in the magnetically-responsive medium, thereby separating the heterogeneous population of cells; and
altering magnetic properties of the magnetically-responsive medium.

35. The method of claim 34, wherein a direction of separation of the heterogeneous population of cells during the step of levitation is perpendicular to a direction of flow of the sample of the heterogeneous population of cells in a magnetically-responsive medium through the microcapillary channel.

36. The method of claim 34, wherein the two magnets are vertically positioned with respect to one another with the microcapillary channel placed therebetween relative to the direction of gravity.

* * * * *

UNITED STATES PATENT AND TRADEMARK OFFICE
CERTIFICATE OF CORRECTION

PATENT NO. : 10,928,404 B2  
APPLICATION NO. : 15/121646  
DATED : February 23, 2021  
INVENTOR(S) : Utkan Demirci et al.

Page 1 of 1

It is certified that error appears in the above-identified patent and that said Letters Patent is hereby corrected as shown below:

In the Specification

Column 7, Line 19, "FIG. Sc" should be --FIG. 5c--.

Column 11, Line 40, "(a=0)" should be --($\alpha$=0)--.

Signed and Sealed this  
Fifteenth Day of June, 2021

Drew Hirshfeld  
*Performing the Functions and Duties of the*  
*Under Secretary of Commerce for Intellectual Property and*  
*Director of the United States Patent and Trademark Office*